(12) United States Patent
Müller

(10) Patent No.: US 7,884,103 B2
(45) Date of Patent: Feb. 8, 2011

(54) N-SULFONYL-α-AMINO-ACID DERIVATIVES

(75) Inventor: Urs Müller, Basel (CH)

(73) Assignee: Syngenta Crop Protection, Inc., Greensboro, NC (US)

(*) Notice: Subject to any disclaimer, the term of this patent is extended or adjusted under 35 U.S.C. 154(b) by 1162 days.

(21) Appl. No.: 10/569,682

(22) PCT Filed: Aug. 27, 2004

(86) PCT No.: PCT/EP2004/009585

§ 371 (c)(1),
(2), (4) Date: Oct. 4, 2006

(87) PCT Pub. No.: WO2005/021490

PCT Pub. Date: Mar. 10, 2005

(65) Prior Publication Data

US 2007/0155748 A1 Jul. 5, 2007

(30) Foreign Application Priority Data

Aug. 29, 2003 (GB) .................................. 0320345.2

(51) Int. Cl.
*C07C 303/00* (2006.01)
*C07C 307/06* (2006.01)
*C07D 249/08* (2006.01)
*C07D 295/00* (2006.01)
*A61K 31/145* (2006.01)

(52) U.S. Cl. ..................... 514/237.5; 514/383; 514/538; 514/602; 514/604; 544/160; 548/262.2; 560/12; 564/93

(58) Field of Classification Search ........................ None
See application file for complete search history.

(56) References Cited

U.S. PATENT DOCUMENTS 6,831,196 B2  12/2004 Sturzebecher et al.

FOREIGN PATENT DOCUMENTS

EP  0176327  2/1986
WO  WO 99/43644  2/1999
WO  WO 01/96286 A2  2/2001

*Primary Examiner*—Fiona T Powers
(74) *Attorney, Agent, or Firm*—James Cueva

(57) ABSTRACT

The invention relates to N-sulfonyl-α-amino-acetic acid derivatives of the general formula (I): including the optical isomers thereof and mixtures of such isomers, wherein $Ar_1$ and $Ar_2$ independently of each other stand for an optionally substituted aryl or heteroaryl group, $R_1$ and $R_2$ stand independently of each other for hydrogen, optionally substituted $C_1$-$C_5$alkyl, optionally substituted $C_2$-$C_5$alkenyl, $C$-$_2C_5$alkynyl or optionally substituted $C_3C_6$Cycloalkyl; $R_3$ designates hydrogen, $C$-$_3C_5$alkenyl, $C_3$-$C_5$ alkynyl or optionally substituted $C_1$-$C_5$alkyl; $R_4$ is optionally substituted $C_1$-$C_5$alkyl, optionally substituted $C$-$_2C_5$alkenyl, $C$-$_2C_5$aklynyl or optionally substituted $C$-$_3C_6$ cycloalkyl; $R_5$ and $R_6$ are independently of each other hydrogen or optionally substituted $C_1$-$C_5$alkyl, optionally substituted $C_2$-$C_5$alkenyl, $C$-$_2C_5$alkynyl or optionally substituted $C_3$-$C_6$cycloalkyl; $R_7$ and $R_8$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl; W designates a bridge selected from —O—, —S—, —SO—, —SO$_2$— or is an —NH— or —N($C_1$-$C_5$alkyl)-bridge; X designates a direct bond or a bridge selected from —O—, —S—, —SO—, —SO$_2$— or is an —NH or —N($C_1C_5$alkyl)-bridge; Y designates —OR$_9$ or NR$_{10}$R$_{11}$; a and b independently of each other stand for a number 1, 2 or 3; and c stands for a number zero, 1 or 2; with $R_9$, $R_{10}$ and $R_{11}$ being defined according to the claims. These compounds possess useful plant protecting properties and may advantageously be employed in agricultural practice for controlling or preventing the infestation of plants by phytopathogenic microorganisms, especially fungi.

(I)

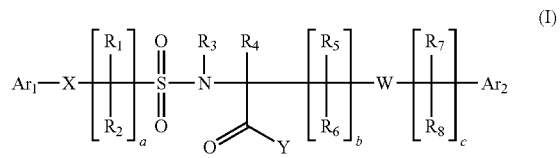

14 Claims, No Drawings

N-SULFONYL-α-AMINO-ACID DERIVATIVES

This application is a 371 of International Application No. PCT/EP2004/009585 filed Aug. 27, 2004, which claims priority to GB 0320345.2 filed Aug. 29, 2003, the contents of which are incorporated herein by reference.

The present invention relates to novel N-sulfonyl-α-amino-acid derivatives of formula I. It further encompasses the preparation of the novel active compounds and to agrochemical compositions comprising at least one of these novel compounds as active ingredient. The invention further relates to the preparation of the said compositions and to the use of the compounds or of the compositions for controlling or preventing the infestation of plants by phytopathogenic microorganisms, especially fungi.

The N-sulfonyl-α-amino-acid derivatives according to the present invention correspond to the general formula I

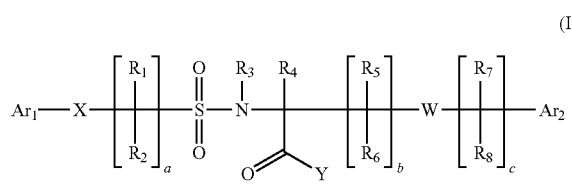

including the optical isomers thereof and mixtures of such isomers, wherein $Ar_1$ and $Ar_2$ independently of each other stand for an optionally substituted aryl or heteroaryl group, $R_1$ and $R_2$ stand independently of each other for hydrogen, optionally substituted $C_1$-$C_5$alkyl, optionally substituted $C_2$-$C_5$alkenyl, $C_2$-$C_5$alkynyl or optionally substituted $C_3$-$C_6$cycloalkyl;

$R_3$ designates hydrogen, $C_3$-$C_5$alkenyl, $C_3$-$C_5$alkynyl or optionally substituted $C_1$-$C_5$alkyl;

$R_4$ is optionally substituted $C_1$-$C_5$alkyl, optionally substituted $C_2$-$C_5$alkenyl, $C_2$-$C_5$alkynyl or optionally substituted $C_3$-$C_6$cycloalkyl;

$R_5$ and $R_6$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl;

$R_7$ and $R_8$ are independently of each other hydrogen or optionally substituted $C_1$-$C_5$alkyl, optionally substituted $C_2$-$C_5$alkenyl, $C_2$-$C_5$alkynyl or optionally substituted $C_3$-$C_6$cycloalkyl;

W designates a bridge selected from —O—, —S—, —SO—, —SO$_2$— or is an —NH— or —N($C_1$-$C_5$alkyl)-bridge;

X designates a direct bond or a bridge selected from —O—, —S—, —SO—, —SO$_2$— or is an —NH— or —N($C_1$-$C_5$alkyl)-bridge;

Y designates —OR$_9$ or NR$_{10}$R$_{11}$;

a and b independently of each other stand for a number 1, 2 or 3; and c stands for a number zero, 1 or 2;

$R_9$ designates hydrogen, optionally substituted $C_1$-$C_5$alkyl, $C_3$-$C_5$alkenyl, $C_3$-$C_5$alkynyl, optionally substituted phenyl;

$R_{10}$ and $R_{11}$ independently of each other stand for hydrogen, $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for a group —NH—CH(R$_{12}$)CO—Z; or $R_{10}$ and $R_{11}$ together form a 5-ring-membered non-aromatic carbocyclic ring; or together form a 6-ring-membered non-aromatic carbocyclic ring which is interrupted by —O—, —S— or —N($C_1$-$C_5$alkyl)-;

$R_{12}$ designates $C_1$-$C_5$alkyl optionally substituted by halogen, $C_1$-$C_5$haloalkyl or aryl which in turn is optionally substituted by halogen, $C_1$-$C_5$alkyl, $C_1$-$C_5$haloalkyl, $C_1$-$C_4$alkoxy, hydroxy or —CN;

Z is —OR$_9$ or NR$_{13}$R$_{14}$;

$R_{13}$ and $R_{14}$ independently of each other stand for hydrogen; $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or $R_{13}$ and $R_{14}$ together form a 5-ring-membered non-aromatic carbocyclic ring; or together form a 6-ring-membered non-aromatic carbocyclic ring which is interrupted by —O—, —S— or —N($C_1$-$C_5$alkyl)-.

More specifically the present invention refers to the N-sulfonyl-α-amino-acid derivatives of formula I wherein $Ar_1$ stands for an aryl group which is optionally substituted with n radicals independently selected from $R_{15}$. $R_{15}$ stands for $C_1$-$C_5$alkyl optionally substituted by halogen, $C_1$-$C_4$alkoxy, NR$_{16}$R$_{17}$, —CO—R$_{18}$ or the acyclic or cyclic ketals and acetals of —CO—R$_{18}$; or stands for a —X-linked aryl which is optionally substituted by halogen, $C_1$-$C_5$alkyl, $C_1$-$C_5$haloalkyl, $C_1$-$C_4$alkoxy, —CN, —NO$_2$, —NR$_{16}$R$_{17}$, —CO—R$_{18}$ or the acyclic or cyclic ketals and acetals of —CO—R$_{18}$; or for an —X-linked 5- or 6-ring-membered heteroaryl group optionally substituted by halogen, $C_1$-$C_5$alkyl, $C_1$-$C_5$haloalkyl, $C_1$-$C_4$alkoxy, —CN, —NO$_2$, —NR$_{16}$R$_{17}$, —CO—R$_{18}$ or the acyclic or cyclic ketals and acetals of —CO—R$_{18}$;

$R_{16}$ and $R_{17}$ independently of each other stand for hydrogen; $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or together form a 5-ring-membered non-aromatic carbocyclic ring; or together form a 6-ring-membered non-aromatic carbocyclic ring which is interrupted by —O— or —N($C_1$-$C_5$alkyl)-;

$R_{18}$ stands for $C_1$-$C_5$alkyl optionally substituted by halogen, $C_1$-$C_4$alkoxy, $C_1$-$C_5$alkylamino, di($C_1$-$C_5$alkyl)amino; aryl which in turn is optionally substituted by halogen, $C_1$-$C_5$alkyl, $C_1$-$C_5$haloalkyl, $C_1$-$C_4$alkoxy, —CN, —$NO_2$, $C_1$-$C_5$alkylamino, di($C_1$-$C_5$alkyl)amino or $C_1$-$C_5$alkylcarbonyl, $C_1$-$C_4$alkoxycarbonyl, $C_1$-$C_5$alkylaminocarbonyl or di($C_1$-$C_5$alkyl)aminocarbonyl; or by a 5- or 6-ring hetero-aromatic ring which in turn is optionally substituted by halogen, $C_1$-$C_5$alkyl, $C_1$-$C_5$haloalkyl $C_1$-$C_4$alkoxy, —CN, —$NO_2$, $C_1$-$C_5$alkylamino, di($C_1$-$C_5$alkyl)amino, $C_1$-$C_5$alkylcarbonyl, $C_1$-$C_4$alkoxycarbonyl, $C_1$-$C_5$alkylaminocarbonyl or di-($C_1$-$C_5$alkyl)aminocarbonyl; or stands for $C_3$-$C_6$cycloalkyl optionally substituted by halogen, hydroxy, =O, $C_1$-$C_4$alkoxy or $C_1$-$C_5$alkylamino, di($C_1$-$C_5$alkyl)amino; or stands for $C_1$-$C_4$alkoxy optionally substituted by halogen, $C_1$-$C_4$alkoxy; $C_1$-$C_5$alkylamino, di($C_1$-$C_5$alkyl)amino; or stands for phenyl which is optionally substituted by halogen, $C_1$-$C_5$alkyl, $C_1$-$C_5$haloalkyl, $C_1$-$C_4$alkoxy, —CN, —$NO_2$, $C_1$-$C_5$alkylamino, di($C_1$-$C_5$alkyl)amino, $C_1$-$C_5$alkylcarbonyl, $C_1$-$C_4$alkoxycarbonyl, $C_1$-$C_5$alkylaminocarbonyl or di-($C_1$-$C_5$alkyl)aminocarbonyl; or stands for a 5- or 6-ring membered heteroaryl comprising nitrogen, oxygen or sulfur as ring members and being optionally substituted by halogen, $C_1$-$C_5$alkyl, $C_1$-$C_5$haloalkyl; $C_1$-$C_4$alkoxy, —CN, —$NO_2$, $C_1$-$C_5$alkylamino, di($C_1$-$C_5$alkyl)amino, $C_1$-$C_5$alkylcarbonyl, $C_1$-$C_4$alkoxycarbonyl, $C_1$-$C_5$alkylaminocarbonyl or di-($C_1$-$C_5$alkyl)aminocarbonyl; or $R_{15}$ stands for $C_3$-$C_6$cycloalkyl, optionally substituted by halogen, hydroxy, =O, $C_1$-$C_4$alkoxy, $NR_{16}R_{17}$; or stands for $C_1$-$C_4$alkoxy optionally substituted by halogen, $C_1$-$C_4$alkoxy, by —X-aryl which is optionally substituted by halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ or the acyclic or cyclic ketals and acetals of —CO—$R_{18}$; by a X-linked-5- or 6-ring-membered heteroaryl group optionally substituted by halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ or the acyclic or cyclic ketals and acetals of —CO—$R_{18}$; or stand for $C_2$-$C_5$alkenyl optionally substituted by halogen or aryl; or stand for $C_2$-$C_5$alkynyl optionally substituted by halogen, tri-$C_1$-$C_4$alkyl-silyl or aryl; or stand for $C_2$-$C_5$alkenyloxy optionally substituted by halogen or aryl; or stand for $C_2$-$C_5$alkynyloxy optionally substituted by halogen, tri-$C_1$-$C_4$alkyl-silyl or aryl; or stand for $C_3$-$C_6$cycloalkoxy optionally substituted by $C_1$-$C_3$alkyl, halogen or $C_1$-$C_4$alkoxy; or stand for halogen; or stand for —$NR_{16}R_{17}$, or stand for —$NR_2$—CO—$R_{16}$; or stand for —$NR_2$—CO—$OR_{16}$; or stand for —$NR_2$—CO—$NR_{16}R_{17}$; or stand for —$NR_2$—CO—$SR_{16}$; or stand for —$NR_2$—CS—$OR_{16}$; or stand for —$NR_2$—CS—$NR_{16}R_{17}$; or stand for —$NR_2$—CS—$SR_{16}$; or stand for —$NR_2$—C(=N—O—$R_{16}$)—S—$OR_{16}$; or stand for —$NR_2$—C(=N—O—$R_{16}$)—$NR_{16}R_{17}$; or stand for —$NR_2$—C(=N—O—$R_{16}$)—$SR_{16}$; or stand for $C_1$-$C_5$alkylthio, $C_1$-$C_5$alkylsulfonyl or $C_1$-$C_5$alkylsulfonyl, optionally substituted by halogen; or stand for —$NR_2$—$SO_2$—$NR_{16}R_{17}$; or stand for nitro, for cyano or for —CS—$NH_2$;

or $Ar_1$ stands for a 5-ring-membered heteroaryl group comprising as ring members 1 to 4 heteroatoms selected from nitrogen, oxygen or sulfur and in which each ring system may not contain more than one oxygen or sulfur atoms and being optionally substituted with n radicals independently selected from $R_{19}$, $R_{19}$ is hydrogen, halogen, $C_1$-$C_5$alkyl, $C_1$-$C_5$haloalkyl, $C_1$-$C_4$alkoxy, —$NR_{16}R_{17}$, —$NO_2$, —CN, —CO—$R_{18}$ or the acyclic or cyclic ketals and acetals of —CO—$R_{16}$; or $Ar_1$ stands for a 6-ring-membered heteroaryl group comprising as ring members 1 to 4 nitrogen atoms, and being optionally substituted with n radicals independently selected from $R_{19}$;

$Ar_2$ stands for an aryl group which is optionally substituted with n radicals independently selected from $R_{20}$, wherein $R_{20}$ is as defined as $R_{15}$, and from one radical $R_{21}$, $R_{21}$ stands for hydrogen; or stands for —X-aryl which is optionally substituted by halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ or the acyclic or cyclic ketals and acetals of —CO—$R_{18}$; or stands for an —X-linked 5-membered aromatic or non-aromatic heterocyclic ring comprising nitrogen, oxygen or sulfur as ring members and being optionally substituted by halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ or the acyclic or cyclic ketals and acetals of —CO—$R_{18}$; or stands for a X-linked 6-membered aromatic or non-aromatic heterocyclic ring comprising nitrogen, oxygen or sulfur as ring members and being optionally substituted by halogen, $C_1$-$C_5$alkyl, $C_1$-$C_5$haloalkyl, $C_1$-$C_4$alkoxy, —ON, —$NO_2$, —$NR_{16}R_{17}$, —CO—$R_{18}$ or the acyclic or cyclic ketals and acetals of —CO—$R_{18}$; or stands for —CO—$R_{18}$ or the acyclic or cyclic ketals and acetals of —CO—$R_{18}$; or stands for —O—CO—$R_{18}$; or stands for —C(=N—O—$R_{16}$)—$R_{18}$;

or $R_{21}$ and one $R_{20}$ together form a 3- or 4-membered non-aromatic bridge forming an annellated ring which may contain a carbonyl function or nitrogen, oxygen or sulfur as ring members and is optionally substituted by $C_1$-$C_3$alkyl;

or $Ar_2$ stands for a 5-ring-membered heteroaryl group comprising as ring members 1 to 4 heteroatoms selected from nitrogen, oxygen or sulfur and in which each ring system may not contain more than 1 oxygen or sulfur atoms and being optionally substituted with n radicals independently selected from $R_{19}$; or stands for a 6-ring-membered heteroaryl group comprising as ring members 1 to 4 nitrogen atoms, and being optionally substituted with n radicals independently selected from $R_{19}$; or stands for a fused bicyclic heteroaryl group comprising as ring members 1 to 4 heteroatoms selected from nitrogen, oxygen or sulfur, and being composed from the 5-ring- or 6-ring-membered heteroaryl groups as defined for $Ar_2$ with an annellated phenyl ring or with an annellated second 6-ring-membered heteroaryl, each ring and the bicyclic heteroaryl being optionally substituted with n radicals independently selected from $R_{19}$.

The number n independently selected is a number between zero and the number of the respective ring members minus the number of ring members and the number of further substituents. Preferably, n is 1. If n is zero, eventually vacant valences of the respective ring are substituted with hydrogen.

$R_1$ and $R_2$ stand independently of each other for hydrogen or $C_1$-$C_5$alkyl optionally substituted by halogen, $C_1$-$C_3$alkoxy or —$NR_{16}R_{17}$; or stand for $C_2$-$C_5$alkenyl optionally substituted by halogen or $C_1$-$C_3$alkoxy; or stand for $C_2$-$C_5$alkynyl; or stand for $C_3$-$C_6$cycloalkyl optionally substituted by halogen, $C_1$-$C_3$alkoxy; $C_1$-$C_3$alkyl or —$NR_{16}R_{17}$;

$R_3$ designates hydrogen, $C_3$-$C_5$alkenyl, $C_3$-$C_5$alkynyl or $C_1$-$C_3$alkyl optionally substituted by $C_1$-$C_3$alkoxy; $C_3$-$C_5$alkenyloxy or $C_3$-$C_5$alkynyloxy;

$R_4$ is $C_1$-$C_5$-alkyl optionally substituted by halogen, $C_1$-$C_3$alkoxy or —$NR_{16}R_{17}$; or is $C_2$-$C_5$alkenyl optionally substituted by halogen or $C_1$-$C_3$alkoxy; or is $C_2$-$C_5$alkynyl; or is $C_3$-$C_6$cycloalkyl optionally substituted by halogen, $C_1$-$C_3$alkoxy or $C_1$-$C_3$alkyl; or $R_5$ and $R_5$ are independently of each other hydrogen or $C_1$-$C_5$alkyl optionally substituted by halogen, $C_1$-$C_3$alkoxy or —$NR_{16}R_{17}$; or are $C_2$-$C_5$alkenyl optionally substituted by halogen or $C_1$-$C_3$alkoxy; or are $C_2$-$C_5$alkynyl; or are $C_3$-$C_6$cycloalkyl optionally substituted by halogen, $C_1$-$C_3$alkoxy; $C_1$-$C_3$alkyl or —$NR_{16}R_{17}$;

$R_7$ and $R_8$ are independently of each other hydrogen or $C_1$-$C_5$alkyl optionally substituted by halogen, $C_1$-$C_3$alkoxy or —$NR_{16}R_{17}$; or are $C_2$-$C_5$alkenyl optionally substituted by halogen or $C_1$-$C_3$alkoxy; or are $C_2$-$C_5$alkynyl; or are $C_3$-$C_6$cycloalkyl optionally substituted by halogen, $C_1$-$C_3$alkoxy; $C_1$-$C_3$alkyl or —$NR_{16}R_{17}$.

In the above definitions "halo" or "halogen" includes fluorine, chlorine, bromine and iodine. The alkyl, alkenyl and alkynyl radicals may be straight-chain or branched. This applies also to the alkyl, alkenyl or alkynyl parts of other alkyl-, alkenyl- or alkynyl-containing groups, such as alkoxy, alkylthio, alkylamino and dialkylamino.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl for example is, depending upon the number of carbon atoms mentioned, cyclopropyl, cyclobutyl, cyclopentyl, cyclohexyl, bicyclohexyl, cycloheptyl, bicycloheptyl, cyclooctyl or bicyclooctyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2-butynyl or octyn-1-yl, depending on the number of carbon atoms present.

A haloalkyl, haloalkenyl, haloalkynyl or halocycloalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, $CH_2CH_2Cl$, $CH_2CH_2F$, $CH_2CHF_2$, $CH_2$—$C$=$CHCl$, $CH$=$CCl_2$, $CH$=$CF_2$, $CH_2$—$C$≡$CCl$, $CH_2$—$C$≡$C$—$CF_3$, chlorocyclohexyl, dichlorocyclohexyl, etc.

Alkoxy thus includes methoxy, ethoxy, propoxy, isopropoxy, n-butyloxy, s-butyloxy, i-butyloxy or t-butyloxy.

$Ar_1$ and $Ar_2$ according to the present invention both present aromatic moieties, belonging to the chemical class of aromatic hydrocarbons or aromatic heterocycles, designated as aryl or heteroaryl.

The definition aryl includes aromatic hydrocarbon ring systems like phenyl, naphthyl, anthracenyl, phenanthrenyl and biphenyl like 1,3-biphenyl and 1,4-biphenyl, with phenyl being preferred. The same definition applies where aryl is part of aryloxy.

Heteroaryl stands for monocyclic aromatic ring systems comprising 1 to 4 heteroatoms selected from N, O and S, where it is understood that for the reasons of complying with the aromatic character of the heteroaryl rings 1 to 4 nitrogen atoms may be present in one ring, but in general not more than one of them may be replaced by oxygen or sulfur. However for the purposes of defining $Ar_2$ heteroaryl includes bicyclic aromatic ring systems comprising an aromatic 5- to 6-membered ring heterocycle condensed with another aromatic 6-membered ring, either an heterocycle or a benzene ring. Where condensed ring systems of more than one ring is intended this is especially pointed out, for example by mentioning condensation, including annellation with benzene rings.

Typical examples for 5-rings, 6-rings and bicyclic condensed systems are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuryl, isobenzothienyl, isobenzofuryl, benzimidazolyl, benzopyrazolyl, indazolyl, benzotriazolyl, benzothiazolyl, benzoisothiazolyl, benzoxazolyl, benzisoxazolyl, quinolinyl, isoquinolinyl, phthalazinyl, purinyl, naphthridinyl, pteridinyl, quinoxalinyl, quinazolinyl and cinnolinyl. Preferred heterocycles are furyl, thienyl, pyrrolyl, imidazolyl, thiazolyl, oxazolyl, isoxazolyl, oxadiazolyl, thiadiazolyl, triazolyl, pyridyl, pyridazinyl, pyrimidinyl, pyrazinyl, indolyl, benzothienyl, benzofuryl, benzopyrazolyl, benzothiazolyl, benzoxazolyl, benzisoxazolyl, quinolinyl, isoquinolinyl and quinazolinyl.

Depending on the position of the heteroaryl group, the heterocyclic ring may be linked to the basic molecular structure via a ring-carbon atom or via a nitrogen-ring atom.

The aryl and heteroaryl groups according to the invention may be unsubstituted or are optionally substituted. Where substituents are indicated according to this invention, the ring structures may carry one or more identical or different substituents. Normally not more than three substituents are present at the same time. Examples of substituents of aryl or heteroaryl groups are: alkyl, alkenyl, alkynyl, cycloalkyl, alkylamino, dialkylamino, cyano, nitro, amino, hydroxy, cycloalkyl-alkyl, aryl, arylalkyl, heteroaryl, heteroaryl-alkyl, phenyl and phenyl-alkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; hydroxy, alkylamino; dialkylamino; carboxyl; alkoxycarbonyl; alkenyloxycarbonyl; or alkynyloxycarbonyl.

Typical examples include 1-naphthyl, 2,3-dichlorophenyl, 2,3-difluorophenyl, 2,4,6-trichlorophenyl, 2,4,6-trifluorophenyl, 2,4-dichlorophenyl, 2,4-difluorophenyl, 2,5-dichlorophenyl, 2,5-difluorophenyl, 2,6-dichlorophenyl, 2-chloro-4-ethoxyphenyl, 2-chloro-4-methoxyphenyl, 2-chlorophenyl, 2-ethoxyphenyl, 2-fluoro-4-chlorophenyl, 2-fluoro-4-ethoxyphenyl, 2-fluoro-4-methoxyphenyl, 2-hexyloxyphenyl, 2-methoxy-4-chlorophenyl, 2-methoxyphenyl, 2-methyl-4-chlorophenyl, 2-naphthyl, 2-trifluoromethyl, 3,4,5-trichlorophenyl, 3,4-di-bromophenyl, 3,4-dichlorophenyl, 3,4-difluorophenyl, 3,4-dimethoxyphenyl, 3,4-dimethylphenyl, 3,5-dimethyl-4-chlorophenyl, 3'4'-dichloro-4-biphenylyl, 3-bromo-4-methylphenyl, 3-bromophenyl, 3-chloro-4-cyanophenyl, 3-chloro-4-ethoxyphenyl, 3-chloro-4-fluorophenyl, 3-chloro-4-methoxyphenyl, 3-chlorophenyl, 3-ethyl-4-chlorophenyl, 3-fluoro-4-ethoxyphenyl, 3-fluoro-4-methoxyphenyl, 3-fluoro-4-methoxyphenyl, 3-methoxy-4-chlorophenyl, 3-methylphenyl, 4-(1,3,4-oxadiazol-2-yl)phenyl, 4-(1-imidazolyl)-phenyl, 4-(1-methyl-methoximinomethyl)-phenyl, 4-(2,6-dimethoxypyrimidin-2-ylthio)-phenyl, 4-(2-cyanopyrid-4-yl)-phenyl, 4-(3-methyl-1,2,4-thiadiazol-4-2-yloxy)phenyl, 4-(3-methyl-1,2,4-thiazol-5-yloxy)-phenyl, 4-(5-ethyl-1,3,4-oxadiazol-2-yl)phenyl, 4-(pyrid-2yloxy)-phenyl, 4'-bromo-4-biphenylyl, 4'-chloro-4-biphenylyl, 4'-cyano-4-biphenylyl, 4'-methyl-4-biphenylyl, 4'-trifluoromethyl-4-biphenylyl, 4-aminocarbonylethoxy-phenyl, 4-aminocarbonylmethylphenyl, 4-aminocarbonyl-phenyl, 4-biphenylyl, 4-bromo-3-chlorophenyl, 4-bromophenyl, 4-chloro-3-cyanophenyl, 4-chloro-3-fluorophenyl, 4-chloro-3-methylphenyl, 4-chloro-3-tri-fluoromethyl-phenyl, 4-chlorophenyl, 4-cyanophenyl, 4-cyclohexylphenyl, 4-ethenylphenyl, 4-ethoxyphenyl, 4-ethylphenyl, 4-ethynyloxyphenyl, 4-ethynylphenyl, 4-fluorophenyl, 4-hexyloxyphenyl, 4-isopropylcarbonylamino-phenyl, 4-isopropylphenyl, 4-iso-propoxyphenyl, 4-methoxy-3-methylphenyl, 4-methoxycarbonyl-phenyl, 4-methoxyphenyl, 4-methylphenyl, 4-methylsulfonyl-phenyl, 4-methylthiophenyl, 4-nitrophenyl, 4-N-morpholinocarbonylaminophenyl, 4-N-morpholinocarbonyloxyethoxy-phenyl, 4-phenoxyphenyl, 4-propargyloxyphenyl, 4-propylphenyl, 4-tert.-butylcarbonylaminophenyl, 4-tert.butylphenyl, 4-trifluoromethoxyphenyl, 4-trifluoromethylphenyl, 5-chloro-thien-2-yl, 5-methyl-fur-2-yl, 5-methylthien-2-yl, 6-benzothienyl, 7-benzothienyl, etc.

Where $R_{21}$ and $R_{20}$ together form a bridge the bridge is normally between vicinal carbon atom of $Ar_2$. Thus annellated ring structures are formed, which may be substituted with one or two lower alkyl groups, preferably methyl. The bridge includes —$(CH_2)_3$—, —$(CH_2)_4$—, —O—$(CH_2)_3$—, —CO—$(CH_2)_3$—, —S—$(CH_2)_3$—, —NH—$(CH_2)_3$—, —O—$(CH_2)_2$—, —O—$(CH_2)_2$—O—, —O—$CH_2$—CH$(CH_3)$—O—, —O—$CH_2$—O—, —CO—$(CH_2)_2$—, —S—$(CH_2)_2$—, —NH—$(CH_2)_2$—, —$CH_2$—O—$CH_2$—, —$CH_2$—CO—$CH_2$—, —$CH_2$—S—$CH_2$—, —$CH_2$—NH—$CH_2$—, —CO—O—$(CH_2)_2$—, —CO—NH—$(CH_2)_2$—, —NH—CO—$(CH_2)_2$—, —$CH_2$—CO—O—$CH_2$—, —CO—S—$(CH_2)_2$—, —NH—CO—$CH_2$—, —O—CO—$(CH_2)_2$—, —$CH_2$—CO—O—, —$CH_2$—O—CO—, —S—CO—$(CH_2)_2$—, —CO—NH—$CH_2$— and —$CH_2$—CO—NH—$CH_2$—, etc. Where the acetals or ketals of —CO—$R_{18}$ are intended the acetals and ketals may appear as —C$(C_1$-$C_4$alkoxy$)_2$-$R_{18}$ or as cyclic structures wherein the former carbonyl carbon atom carries a dioxoalkylene bridge of the type —O—$C_1$-$C_3$alkylene-O— which optionally may be branched, including —O—$CH_2$—O—, —O—CH$(CH_3)$—O—, —O—$(CH_2)_2$—O—, —O—$(CH_2)_3$—O—, —O—$CH_2$—CH$(CH_3)$—O—, and the like.

Where $R_{16}$ and $R_{17}$ together with the nitrogen binding the two radicals may form a non-aromatic carbocyclic ring this radical stands for pyrrolidine, piperidine, morpholine or thiomorpholine ring, which may be substituted by one or two methyl groups.

The presence of at least one asymmetric carbon atom in the compounds of formula I means that the compounds may occur in optically isomeric, diastereomeric and enantiomeric forms. As a result of the presence of a possible aliphatic C═C double bond, geometric isomerism may also occur. Formula I is intended to include all those possible isomeric forms and mixtures thereof. Where no specific isomer is specified the mixtures of diastereomers, enantiomers or the racemate are meant, as obtainable from the disclosed synthesis methods. The optical isomers, diastereomers and enantiomers of formula I may be obtained in pure form either by isolation from the mixture by suitable separation methods, which are known in the art, or may be obtained by stereoselective synthesis methods.

In another embodiment of the invention, subgroups of compounds of formula I are those wherein $Ar_1$ stands for optionally substituted aryl group; or $Ar_1$ is optionally substituted phenyl; or $Ar_2$ stands for optionally substituted aryl; or $Ar_2$ is optionally substituted phenyl; or $Ar_1$ and $Ar_2$ independently of each other stand for optionally substituted phenyl; or the optional substituents $R_{15}$ of $Ar_1$ are preferably selected from the group comprising halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN and —CO—$R_{18}$; or the optional substituents $R_{20}$ of $Ar_2$ are preferably selected from the group comprising halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN, —CO—$R_{18}$, —$NR_{16}R_{17}$, —$NR_2$—CO—$R_{16}$, —$NR_3$—CO—$OR_{16}$, —$NR_2$—CO—$NR_{16}R_{17}$, —$NR_2$—CO—$SR_{16}$, —$NR_2$—CS—$OR_{16}$, —$NR_2$—CS—$NR_{16}R_{17}$, —$NR_2$—CS—$SR_{16}$, $C_1$-$C_5$alkylthio, $C_1$-$C_5$alkylsulfinyl, $C_1$-$C_5$alkylsulfonyl, $C_1$-$C_5$haloalkylthio, $C_1$-$C_5$haloalkylsulfinyl, $C_1$-$C_5$haloalkylsulfonyl, —$NR_2$—$SO_2$—$NR_{16}R_{17}$, nitro, cyano and —CS—$NH_2$; or the optional substituents $R_{15}$ and $R_{20}$ of $Ar_1$ and $Ar_2$ are selected from the group comprising $C_1$-$C_5$alkyl, $C_1$-$C_5$haloalkyl, $C_1$-$C_4$alkoxy, $C_1$-$C_4$haloalkoxy and $C_3$-$C_6$cycloalkyl; or the optional substituents $R_{15}$ and $R_{20}$ of $Ar_1$ and $Ar_2$ are selected from the group comprising bromo, chloro, fluoro, iodo, cyano, hydroxy, amino, nitro, methyl, ethyl, propyl, isopropyl, methoxy, ethoxy, propoxy, isopropoxy, allyloxy, propargyloxy, benzyloxy, trifluoromethyl, trifluoromethoxy, 2-cyano-2-methyl-butyloxy, methylsulfonyl, methylsulfinyl, methylthio, cyclopentyl, cyclohexyl, aminocarbonylmethyl, methoximinoethyl, aminocarbonyl, butylcarbonylamino, tert-butylcarbonylamino, triazol-1-ylmethyl, 1,2,4-triazol-1-ylmethyl, N-morpholinocarbonylamino, aminocarbonyloxyethoxy, morpholinocarbonyloxyethoxy and cyanopyridyloxyethoxy; or the optional substituents $R_{15}$ and $R_{20}$ of $Ar_1$ and $Ar_2$ are selected from the group comprising bromo, chloro, fluoro, methyl, ethyl, methoxy, ethoxy, trifluoromethyl and trifluoromethoxy; or the optional substituent $R_{21}$ on $Ar_2$ is selected from optionally substituted phenyl, optionally substituted imidazolyl, optionally substituted thiazolyloxy, optionally substituted pyridyloxy, optionally substituted pyridyl, optionally substituted pyrimidinyloxy, optionally substituted pyrimidinyl, optionally substituted oxadiazolyl, optionally substituted triazolyl, optionally substituted pyrazolyl, optionally substituted oxadiazolyloxy, optionally substituted triazolyloxy and optionally substituted pyrazolyloxy; or the optional substituent $R_{21}$ on $Ar_2$ is selected from halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ and the acyclic or cyclic ketals and acetals of —CO—$R_{18}$; or the optional substituent $R_2$, on $Ar_2$ is selected from —CO—$R_{18}$, —O—CO—$R_{18}$, optionally substituted phenyl, optionally substituted phenoxy, optionally substituted imidazolyl, optionally substituted imidazolyloxy, optionally substituted thiazolyloxy, optionally substituted thiazolyl, optionally substituted thiadiazolyloxy, optionally substituted thiadiazolyl, optionally substituted pyridyloxy, optionally substituted pyridyl, optionally substituted pyrimidinyloxy, optionally substituted pyrimidinyl, optionally substituted oxadiazolyl, optionally substituted oxadiazolyloxy, optionally substituted triazolyl, optionally substituted pyrazolyl, optionally substituted triazolyloxy and optionally substituted pyrazolyloxy; or the optional substituent $R_{21}$ on $Ar_2$ is selected from —CO—$C_1$-$C_5$alkyl, —O—CO—$C_1$-$C_5$alkyl and —CO—$C_1$-$C_4$alkoxy; or the optional substituent $R_2$, on $Ar_2$ is selected from aminocarbonyl, dimethylaminocarbonyl, acetyl, propionyl, acetoxy, methoxycarbonyl, ethoxycarbonyl, benzoyl, methoximinoethyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dichloropyridyloxy), 2-(4,6-dimethoxypyrimidinylthio), 2-oxadiazolyl, 2-(5-methyloxadiazolyl), 2-(5-ethyl-oxadiazolyl), 1-triazolyl, 1-pyrazolyl, 1-(3,4-dimethylpyrazolyl), 4-(2-methylthiazolyl), 2-(1,3,4-oxydiazolyl), N-pyrrolidin-2-onyl, and 2-quinoxalinyl, or $R_1$, $R_2$, $R_5$, $R_6$, $R_7$ and $R_8$ independently of each other stand for hydrogen or methyl; or $R_1$ and $R_5$ are independently of each other $C_1$-$C_5$alkyl and $R_2$ and $R_6$ are hydrogen; or $R_3$ is hydrogen or $C_1$-$C_5$alkyl optionally substituted with $C_1$-$C_4$alkoxy, $C_3$-$C_4$alkenyloxy, or $C_3$-$C_4$alkynyloxy; or $R_3$ is hydrogen, $C_1$-$C_5$alkyl or $C_1$-$C_4$alkoxy-$C_1$-$C_5$alkyl; or $R_4$ is hydrogen or $C_1$-$C_5$alkyl optionally substituted with halogen, $C_1$-$C_3$alkoxy, $C_1$-$C_3$alkylamino or di-$C_1$-$C_3$alkylamino; or $R_4$ is hydrogen, $C_1$-$C_5$alkyl or $C_1$-$C_5$haloalkyl or $R_4$ is $C_1$-$C_5$alkyl or $C_1$-$C_5$haloalkyl; or Y stands for O—$R_9$, where $R_9$ is hydrogen, substituted $C_1$-$C_5$alkyl; $C_3$-$C_5$alkenyl, $C_3$-$C_5$alkynyl, phenyl, 4-halogenophenyl;

$R_{10}$ and $R_{11}$ independently of each other stand for hydrogen; $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for a group —NH—CH($R_{12}$)CO—Z; or $R_{10}$ and $R_{11}$ together form a 5-ring-membered non-aromatic carbocyclic ring; or together form a 6-ring-membered non-aromatic carbocyclic ring which is interrupted by —O—, —S— or —N($C_1$-$C_5$alkyl)-;

$R_{12}$ designates $C_1$-$C_5$alkyl optionally substituted by halogen, $C_1$-$C_5$haloalkyl or aryl which in turn is optionally substituted by halogen, $C_1$-$C_5$alkyl, $C_1$-$C_5$haloalkyl, $C_1$-$C_4$alkoxy, hydroxy or —CN;

Z is —$OR_9$; $NR_{13}R_{20}$; $R_{13}$ and $R_{20}$ independently of each other stand for hydrogen; $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or $R_{13}$ and $R_{20}$ together form a 5-ring-membered non-aromatic carbocyclic ring; or together form a 6-ring-membered non-aromatic carbocyclic ring which is interrupted by —O—, —S— or —N($C_1$-$C_5$alkyl)-;

W is —O—; or

X is a direct bond; or the suffixes (a) and (b) designate the number 1; or the suffix (c) stands for the number zero.

In a further embodiment of the invention, the subgroup of formula I is wherein $Ar_1$ and $Ar_2$ independently of each other stand for optionally substituted phenyl; and the optional substituents $R_{15}$ of $Ar_1$ are preferably selected from the group comprising halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN and —CO—$R_{18}$; and the optional substituents $R_{20}$ of $Ar_2$ are preferably selected from the group comprising halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN, —CO—$R_{18}$, —$NR_{16}R_{17}$, —$NR_2$—CO—$R_{16}$, —$NR_3$—CO—$OR_{16}$, —$NR_2$—CO—$NR_{16}R_{17}$, —$NR_2$—CO—$SR_{16}$, —$NR_2$—CS—$OR_{16}$, —$NR_2$—CS—$NR_{16}R_{17}$, —$NR_2$—CS—$SR_{16}$, $C_1$-$C_5$alkylthio, $C_1$-$C_5$alkylsulfinyl, $C_1$-$C_5$alkylsulfonyl, $C_1$-$C_5$haloalkylthio, $C_1$-$C_5$haloalkylsulfinyl, $C_1$-$C_5$haloalkylsulfonyl, —$NR_2$—$SO_2$—$NR_{16}R_{17}$, nitro, cyano and —CS—$NH_2$; and the optional substituent $R_{21}$ on $Ar_2$ is selected from optionally substituted phenyl, optionally substituted imidazolyl, optionally substituted thiazolyloxy, optionally substituted pyridyloxy, optionally substituted pyridyl, optionally substituted pyrimidinyloxy, optionally substituted pyrimidinyl, optionally substituted oxadiazolyl, optionally substituted triazolyl, optionally substituted pyrazolyl, optionally substituted oxadiazolyloxy, optionally substituted triazolyloxy and optionally substituted pyrazolyloxy.

Further preferred subgroups are those wherein

A) $Ar_1$ and $Ar_2$ independently stand for optionally substituted aryl groups; and the optional substituents $R_{15}$ of $Ar_1$ are preferably selected from the group comprising halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN and —CO—$R_{18}$; and the optional substituents $R_{20}$ of $Ar_2$ are preferably selected from the group comprising halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN, —CO—$R_{18}$, —$NR_{16}R_{17}$, —$NR_2$—CO—$R_{16}$, —$NR_3$—CO—$OR_{16}$, —$NR_2$—CO—$NR_{16}R_{17}$, —$NR_2$—CO—$SR_{16}$, —$NR_2$—CS—$OR_{16}$, —$NR_2$—CS—$NR_{16}R_{17}$, —$NR_2$—CS—$SR_{16}$, $C_1$-$C_5$alkylthio, $C_1$-$C_5$alkylsulfinyl, $C_1$-$C_5$alkylsulfonyl, $C_1$-$C_5$haloalkylthio, $C_1$-$C_5$haloalkylsulfinyl, $C_1$-$C_5$haloalkylsulfonyl, —$NR_2$—$SO_2$—$NR_{16}R_{17}$, nitro, cyano and —CS—$NH_2$; and the optional substituent $R_{21}$ on $Ar_2$ is selected from halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ and the acyclic or cyclic ketals and acetals of —CO—$R_{18}$; —O—CO—$R_{18}$, optionally substituted phenyl, optionally substituted imidazolyl, optionally substituted thiazolyloxy, optionally substituted pyridyloxy, optionally substituted pyridyl, optionally substituted pyrimidinyloxy, optionally substituted pyrimidinyl, optionally substituted oxadiazolyl, optionally substituted triazolyl, optionally substituted pyrazolyl, optionally substituted oxadiazolyloxy, optionally substituted triazolyloxy and optionally substituted pyrazolyloxy; and $R_1$, $R_2$, $R_5$, $R_6$, $R_7$ and $R_8$ independently of each other are hydrogen or methyl; and $R_3$ is hydrogen or $C_1$-$C_5$alkyl optionally substituted with $C_1$-$C_4$alkoxy, $C_3$-$C_4$alkenyloxy, or $C_3$-$C_4$alkynyloxy; and $R_4$ is hydrogen or $C_1$-$C_5$alkyl optionally substituted with halogen, $C_1$-$C_3$alkoxy, $C_1$-$C_3$alkylamino or di-$C_1$-$C_3$alkylamino; and W is —O—; and Y is $OR_9$, where $R_9$ is hydrogen, $C_1$-$C_5$alkyl; $C_3$-$C_5$alkenyl, $C_3$-$C_5$alkynyl, 4-halogenophenyl or Y is $NR_{10}R_{11}$ and $R_{10}$ and $R_{11}$ independently of each other, stand for hydrogen; $C_1$-$C_5$alkyl, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl; or stand for $C_3$-$C_5$alkynyl; or stand for a group —NH—CH($R_{12}$)CO—Z; or $R_{10}$ and $R_{11}$, together form a 5-ring-membered non-aromatic carbocyclic ring; or together form a 6-ring-membered non-aromatic carbocyclic ring which is interrupted by —O—, —S— or —N($C_1$-$C_5$alkyl)-;

$R_{12}$ designates $C_1$-$C_5$alkyl;

Z is —$OR_9$, $NR_{13}R_{14}$; $R_{13}$ and $R_{14}$ independently of each other, stand for hydrogen; $C_1$-$C_5$alkyl, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl; or stand for $C_3$-$C_5$alkynyl; or stand for a group —NH—CH($R_{12}$)CO—Y; or $R_{13}$ and $R_{14}$ together form a 5-ring-membered non-aromatic carbocyclic ring; or together form a 6-ring-membered non-aromatic carbocyclic ring which is interrupted by —O—, —S— or —N($C_1$-$C_5$alkyl)-;

X is a direct bond; and the suffixes (a) and (b) designate the number 1; and the suffix (c) stands for the number zero; or wherein B) $Ar_1$ and $Ar_2$ independently of each other stand for optionally substituted phenyl; and the optional substituents $R_{15}$ and $R_{20}$ of $Ar_1$ and $Ar_2$ are selected from the group comprising $C_1$-$C_5$alkyl, $C_1$-$C_5$haloalkyl, $C_1$-$C_4$alkoxy, $C_1$-$C_4$haloalkoxy and $C_3$-$C_6$cycloalkyl; and the optional substituent $R_{21}$ on $Ar_2$ is selected from —CO—$C_1$-$C_5$alkyl, —CO—$C_1$-$C_4$alkoxy, —O—CO—$C_1$-$C_5$alkyl, optionally substituted phenyl, optionally substituted phenoxy, optionally substituted imidazolyl, optionally substituted imidazolyloxy, optionally substituted thiazolyl-oxy, optionally substituted thiazolyl, optionally substituted thiadiazolyloxy, optionally substituted thiadiazolyl, optionally substituted pyridyloxy, optionally substituted pyridyl, optionally substituted pyrimidinyloxy, optionally substituted pyrimidinyl, optionally substituted oxadiazolyl, optionally substituted oxadiazolyloxy, optionally substituted triazolyl, optionally substituted pyrazolyl, optionally substituted triazolyloxy and optionally substituted pyrazolyloxy; and $R_1$ and $R_5$ are independently $C_1$-$C_5$alkyl and $R_2$ and $R_6$ are hydrogen; and $R_3$ is hydrogen, $C_1$-$C_5$alkyl or $C_1$-$C_4$alkoxy-$C_1$-$C_5$alkyl; and $R_4$ is $C_1$-$C_5$alkyl or $C_1$-$C_5$haloalkyl; and W is —O—; and Y is $OR_9$, where $R_9$ is hydrogen, $C_1$-$C_5$alkyl; $C_3$-$C_5$alkenyl, $C_3$-$C_5$alkynyl, 4-halogenophenyl;

X is a direct bond; and the suffixes (a) and (b) designate the number 1; and the suffix (c) stands for the number zero; or wherein C) $Ar_1$ and $Ar_2$ independently of each other stand for optionally substituted phenyl; and the optional substituents $R_{15}$ and $R_{20}$ of $Ar_1$ and $Ar_2$ are selected from the group comprising bromo, chloro, fluoro, iodo, cyano, hydroxy, amino, nitro, methyl, ethyl, propyl, isopropyl, methoxy, ethoxy, propoxy, isopropoxy, allyloxy, propargyloxy, benzyloxy, trifluoromethyl, trifluoromethoxy, 2-cyano-2-methyl-butyloxy, methylsulfonyl, methylsulfinyl, methylthio, cyclopentyl, cyclohexyl, aminocarbonylmethyl, methoximinoethyl, aminocarbonyl, butylcarbonylamino, tert-butylcarbonylamino, triazol-1-ylmethyl, 1,2,4-triazol-1-ylmethyl, N-morpholinocarbonylamino, aminocarbonyloxy-ethoxy, morpholinocarbonyloxyethoxy and cyanopyridyloxyethoxy; and the optional substituent $R_{21}$ on $Ar_2$ is selected from aminocarbonyl, dimethylaminocarbonyl, acetyl, propionyl, acetoxy, methoxycarbonyl, ethoxycarbonyl, benzoyl, methoximinoethyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dichloropyridyloxy), 2-(4,6-dimethoxypyrimidinylthio), 2-oxadiazolyl, 2-(5-methyl-oxadiazolyl), 2-(5-ethyl-oxadiazolyl), 1-triazolyl, 1-pyrazolyl, 1-(3,4-dimethylpyrazolyl), 4-(2-methylthiazolyl), 2-(1,3,4-oxydiazolyl), N-pyrrolidin-2-onyl, and 2-quinoxalinyl, and $R_1$ and $R_5$ are independently $C_1$-$C_5$alkyl and $R_2$ and $R_6$ are hydrogen; and $R_3$ is hydrogen, $C_1$-$C_5$alkyl or $C_1$-$C_4$alkoxy-$C_1$-$C_5$alkyl; and $R_4$ is $C_1$-$C_5$alkyl or $C_1$-$C_5$haloalkyl; and W is —O—; and Y is $OR_9$, where $R_9$ is hydrogen, $C_1$-$C_5$alkyl; $C_3$-$C_5$alkenyl, $C_3$-$C_5$alkynyl, 4-halogenophenyl;

X is a direct bond; and the suffixes (a) and (b) designate the number 1; and the suffix (c) stands for the number zero; or wherein D) $Ar_1$ and $Ar_2$ independently of each other stand for optionally substituted phenyl; and the optional substituents $R_{15}$ and $R_{20}$ of $Ar_1$ and $Ar_2$ are selected from the group comprising bromo, chloro, fluoro, methyl, ethyl, methoxy, ethoxy, trifluoromethyl and trifluoromethoxy;

and the optional substituent $R_{21}$ on $Ar_2$ is selected from aminocarbonyl, acetyl, methoxycarbonyl, ethoxycarbonyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dimethoxypyrimidinylthio), 2-oxadiazolyl, 2-(5-methyl-oxadiazolyl), 2-(5-ethyl-oxadiazolyl), 1-(1,2,4-triazolyl), 1-pyrazolyl, 4-(2-methylthiazolyl), 2-(1,3,4-oxydiazolyl), and N-pyrrolidin-2-onyl, and $R_1$ and $R_5$ are methyl and $R_2$ and $R_6$ are hydrogen; and $R_3$ is hydrogen, methyl, ethyl, propyl, ethoxymethyl or methoxymethyl, and $R_4$ is methyl, ethyl, propyl or fluoromethyl; and W is —O—; and Y is $OR_9$, where $R_9$ is hydrogen, $C_1$-$C_5$alkyl or halogenophenyl, or Y is $NR_{10}R_{11}$;

X is a direct bond; and the suffixes (a) and (b) designate the number 1; and the suffix (c) stands for the number zero.

In particular, $R_9$ is methyl, ethyl, propyl, isopropyl, n-butyl, iso-butyl, tert.-butyl, 4-chlorophenyl, or 2-methylprop-1-yl;

$R_{10}$ and $R_{11}$, are hydrogen, methyl, ethyl, methoxy, ethoxy, 4-methoxyphenyl, 4-methoxybenzyl, 4-chlorophenyl, propargyl, 1-phenyleth-1-yl, 2-(3,4-dimethyoxy)eth-1-yl;

preferably, if $R_{10}$ and $R_{11}$ together form a 5- or 6-ring-membered ring, said ring is a pyrrolidine ring, a morpholine ring or a piperidine ring.

In a further embodiment of the invention, the compound of formula I is a compound of formula Ia

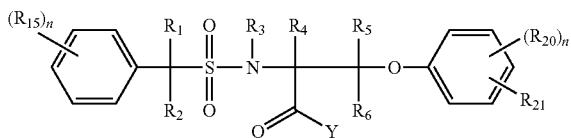

(Ia)

wherein $R_1$, $R_2$, and $R_5$ are hydrogen or methyl;

$R_3$ is hydrogen, methyl, ethoxymethyl;

$R_4$ is methyl, ethyl, propyl, isopropyl, fluoromethyl;

$R_6$ is hydrogen, methyl or ethyl;

$R_{15}$ is hydrogen, fluoro, chloro, bromo, iodo, more specifically, 2-fluoro, 4-chloro or 4-fluoro;

$R_{20}$ is hydrogen, 3-methyl, 4-methyl, 4-isopropyl, 4-propen-1-yl, 4-propin-1-yl, 4-cyano, 4-hydroxy, 3-methoxy, 4-methoxy, 4-ethoxy, 4-methylthio, 4-methylsulfonyl, 4-trifuoromethyl, 4-fluoro, 2-chloro, 3-chloro, 4-chloro, 4-bromo, 4-iodo, 2,3-dichloro, 3,4-dichloro or 2,4-dichloro;

$R_{21}$ is hydrogen, aminocarbonyl, dimethylaminocarbonyl, acetyl, propionyl, acetoxy, methoxycarbonyl, ethoxycarbonyl, benzoyl, methoximinoethyl, 1-imidazolyl, 5-(3-methyl-1,2,4-thiadiazolyloxy), 2-pyridyl, 2-pyridyloxy, 4-pyrimidinyl, 4-(4-thiaimidazolyloxy), 2-(3,5-dichloropyridyloxy), 2-(4,6-dichloropyridyloxy), 2-(4,6-dimethoxypyrimidinylthio), 2-oxadiazolyl, 2-(5-methyl-oxadiazolyl), 2-(5-ethyl-oxadiazolyl), 1-triazolyl, 1-pyrazolyl, 1-(3,4-dimethylpyrazolyl), 1-(3,5-dimethylpyrazolyl), 4-(2-methylthiazolyl), 1-(4-trifuoromethylthiazolyloxy), 2-(1,3,4-oxydiazolyl), N-pyrrolidin-2-onyl, and 2-quinoxalinyl;

Y is hydrogen, hydroxy, methoxy, ethoxy, isopropyloxy, 4-chlorophenyloxy, amino, methylamino, ethylamino, n-butylamino, dimethylamino, methylmethoxyamino, propargylamino, 4-methoxyphenylamino, 4-chlorophenylamino, 1-phenylethylamino, morpholino, 4-methoxybenzylamino, 3,4-dimethoxyphenethylamino.

Preferred individual compounds are:

2, N-dimethyl-2-phenylmethanesulfonylamino-3-(-[1,2,4]triazol-1-yl-phenoxy)-propionamide, 2-methyl-2-phenylmethanesulfonylamino-3-(4-[1,2,4]triazol-1-yl-phenoxy)-propionic acid methyl ester, 2-methyl-2-phenylmethanesulfonylamino-3-(4-[1,2,4]triazol-1-yl-phenoxy)-propionamide, 2-methyl-2-phenylmethanesulfonylamino-3-(4-[1,2,4]triazol-1-yl-phenoxy)-propionic acid, N-(4-chloro-phenyl)-2-methyl-2-phenylmethanesulfonylamino-3-(4-[1,2,4]triazol-1-yl-phenoxy)-propionamide, N-(3-trifluoro-phenyl)-2-methyl-2-phenylmethanesulfonylamino-3-(4-[1,2,4]triazol-1-yl-phenoxy)-propionamide, N-(1-phenyl-ethyl)-2-methyl-2-phenylmethanesulfonylamino-3-(4-[1,2,4]triazol-1-yl-phenoxy)-propionamide, N-[2-(3,4-dimethoxy-phenyl)-ethyl]-2-methyl-2-phenylmethanesulfonylamino-3-(4-[1,2,4]triazol-1-yl-phenoxy)-propionamide, 3-(4-ethoxy-phenoxy)-2,N-dimethyl-2-phenylmethanesulfonylamino-propionamide, 3-(4-thoxy-phenoxy)-2-methyl-N-(1-phenyl-ethyl)-2-phenylmethanesulfonylamino-propionamide, 3-(4-ethoxy-phenoxy)-2-methyl-N-(4-methoxy-benzyl)-2-phenylmethanesulfonylamino-propionamide, 2-(4-ethoxy-phenoxymethyl)-2-phenylmethanesulfonylamino-butyramide, 3-(4-ethoxy-phenoxy)-2-methyl-N-[2-(3,4-dimethoxy-phenyl)-ethyl]-2-phenylmethanesulfonylamino-propionamide, 3-(4-ethoxy-phenoxy)-2,N,N-trimethyl-2-phenylmethanesulfonylamino-propionamide, 3-(4-ethoxy-phenoxy)-2-methyl-2-phenylmethanesulfonylamino-N-prop-2-ynyl-propionamide, 3-(4-ethoxyphenoxy)-2-methyl-2-phenylmethanesulfonylamino-1-morpholin-4-yl-propan-1-one, 3-(4-ethoxy-phenoxy)-N-methoxy-2,N-dimethyl-2-phenylmethanesulfonylamino-propionamide, N-methoxy-2-methyl-2-phenylmethanesulfonylamino-3-(4-[1,2,4]triazol-1-yl-phenoxy)-propionamide, N-(-1-ethynyl-cyclohexyl)-2-methyl-2-phenylmethane-sulfonylamino-3-(4-[1,2,4]triazol-1-yl-phenoxy)-propionamide, and 3-(4-ethoxy-phenoxy)-2-methyl-2-phenylmethanesulfonylamino-propionic acid methyl ester.

Surprisingly, with developing the compounds of formula I a new type of microbiocides has been provided which satisfies to a greater extend the need for an agent for controlling phytopathogenic microorganisms on crop plants having a high level of activity, paired with long lasting effective protection.

The compounds of formula I and the respective starting materials may be obtained according to the processes of Schemes 1 to 6.

Scheme 1:

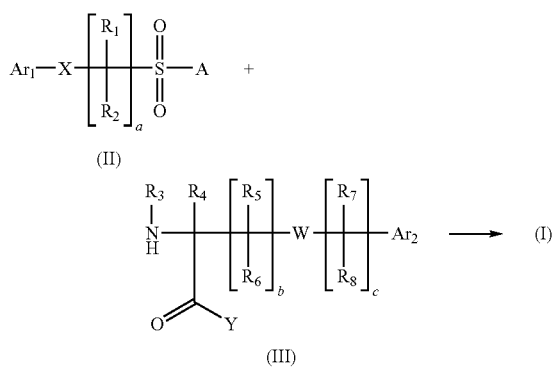

wherein $Ar_1$, $Ar_2$, a, b, c, W Y and $R_1$ to $R_8$, are defined as under formula I, and A stands for a leaving group like an anhydride, i.e. —O—$SO_2$—$(CR_1R_2)_a$—X—$Ar_1$ or —O—CO—$C_1$-$C_5$alkyl, but preferably for halogen, especially bromine or more preferably chlorine.

such as acetone and methylethylketone, halogenated hydrocarbons such as chloroform, carbontetrachloride, dichloromethane, dichloro-ethane, aromatic hydrocarbons such as toluene or xylene, ethers such as t-butyl-methyl-ether, diethyl-ether, tetrahydrofuran and dioxane. The reaction is performed preferentially in the presence of a base and a catalyst. Typical bases include tertiary amines such as trimethylamine, triethylamine, diisopropylethylamine, dimethyl-aniline, diazabi-cyclooctane and N-methylmorpholine, aromatic amines such pyridine and quinoline as well as inorganic bases such as alkaline bicarbonates or -carbonates. Typical salts are for example sodium and potassium bicarbonate and sodium, potassium or cesium carbonate. Suitable catalysts such as N,N-dialkyl- or cycloalkyl-aminopyridines, like e.g. 4-N,N-dimethylaminopyridine, may improve the yield.

The substituents $R_3$ may be introduced into the final active ingredients when starting from the subgroup compounds of formula I wherein $R_3$ is hydrogen, by reacting them e.g. with an alkylating agent $R_3$-A' wherein A' designates a leaving group, preferably a halogen atom, e.g. bromo or chloro. Suitable alkylating agents thus include suitably substituted alkylhalides or alkyl-O-sulfonates, e.g. or alkoxy-alkylhalides. On the other hand, when introducing $R_3$ with the starting compounds of formula III, alkylating of the compounds of the subgroup of formula III, wherein $R_3$ is hydrogen, may be achieved in a similar way by any commonly known alkylation method. Such alkylation prior to sulfonylation with a compound of formula II, as alternative to converting $R_3$ within the final products of formula I, allows to introduce a wide variety of radicals $R_3$ while leaving the choice to decide at which stage such optional conversion is preferably performed.

α-Amino-acid derivatives of formula III may easily be prepared by the so-called Strecker—Synthesis according to Scheme 2 as described e.g. generically in any textbook on organic chemistry, or in a procedure disclosed in the patent literature (EP-A-953565-A; Nihon Noyaku or U.S. Pat. No. 3,529,019, Colgate-Palmolive) starting from the corresponding ketone of formula IV.

Scheme 2

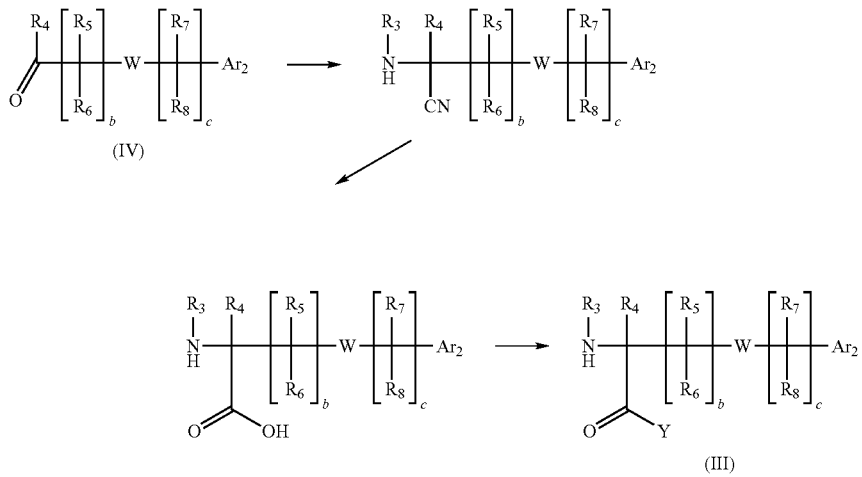

The compounds of formula I may be prepared by sulfonylation of an α-amino-acid derivative of formula III with a sulfonyl-halide/anhydride of formula II wherein A is a leaving group, Suitable solvents for this reaction include ketones, Preparation of the ketones/intermediate aminonitriles are described in patent application nos. GB 0214116.6 and PCT/EP03/06482, which are incorporated by reference for all useful purposes.

Further methods to prepare sulfonylation agent of formula II are known to the artisan. General ways of preparing such compounds are e.g. described in Houben Weyl, Vol. E11, p 1067 ff (1985).

Another synthesis to prepare compounds of formula I is described in Scheme 3.

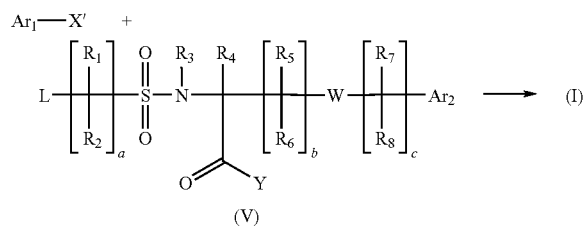

Compounds of formula (V) wherein $Ar_2$, a, b, c, W, Y and $R_1$ to $R_8$ are defined as under formula I and L is a leaving group such as e.g. halogen, preferably chlorine, bromine or iodine or a sulfonyloxy group such a e.g. methylsulfonyloxy-, toluylsulfonyloxy- or trifluoro-methylsulfonyloxy-group, is coupled with a compound of formula $Ar_1$—X' wherein X' is either an anionic radical species of X such as $O^-$, $S^-$, $SO^-$, $SO_2^-$ combined with an alkaline- or earthalkaline-metal cation as counterion or is defined as X—H such as OH, SH, $NHR_3$. In this case the reactions are generally carried out in the presence of a base such as alkaline-, earthalkaline-carbonates or hydrogencarbonates such e.g. sodium or potassium-carbonate, sodium or potassium-hydrogen-carbonate, cesium-carbonate or an agent capable of scavenging the formed acid.

α-Aminoacids of formula (III) wherein $Ar_1$, $Ar_2$, a, b, c, W, Y and $R_1$ to $R_8$, are defined as under formula I, may also be prepared by adaptation of methods developed by Seebach (*Angew. Chem. Int. Ed.* 1996, 35, 2708-2748) as described in Scheme 4. The methods described by Seebach allow both the preparation of racemic and of enantiomerically pure aminoacids of either absolute configuration.

Scope and limitations with respect of stereochemistry and the substituents are well known from the literature. The symbol T in formula (VI) designates a protecting group such as the t-butyloxycarbonyl- or benzyloxycarbonyl-groups, often referred to as (BOC)— or (Z)-groups. L designate a leaving group as defined above. Consecutive alkylation of compounds (VI), which may be either racemic or a pure enantiomer of either configuration yields, following the rules elaborated by Seebach, through the intermediate compounds (IX) and (X) compounds (III) in racemic form or as pure enantiomeres of either configuration.

Yet another way to prepare intermediate amino acid derivatives of formula (III) is described in Scheme 5.

Alkylation of malonic-acid derivatives of formula (XI), where R stands for $C_1$-$C_5$-alkyl, preferrably for methyl, with compounds (VIII), which themselves may be prepared as described e.g. in Acta Chemica Scandinavica, 53(1), 41-47 (1999) leads to compounds (XII) were $Ar_2$, $R_5$-$R_8$, b, c and W are defined as above. Hydrolysis of compounds of formula (XII) by alkali- or earthalkali-bases in solvents like alcohols with addition of water gives the mono-ester derivatives of formula (XIII). In analogy to methods described in the literature (F. Björkling et al. *Tetrahedron* 1985, 41(7), 1347) enantiomerically pure compounds of formula (XIII) may be obtained by kinetic resolution using ester hydrolysing enzymes such as esterases or more specifically pig liver esterases. The racemic or enantiomerically-pure intermediates of formula (XIII) are then transformed to the compounds of formula (XIV) or (XV) by a Curtius rearrangement as e.g. described by K. Ninomiya, T. Shiori, S. Yamada, *Tetrahedron* 1974, 30, 2151. By transformations well known in the field of amino-acid chemistry intermediate compounds XIV respectively XIV lead to compounds (III).

Scheme 4:

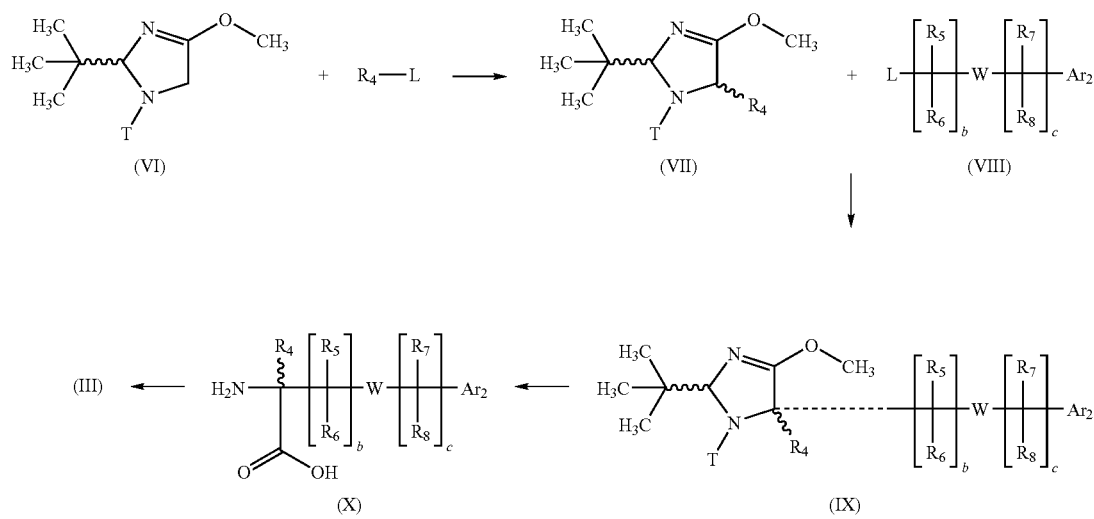

Scheme 5:

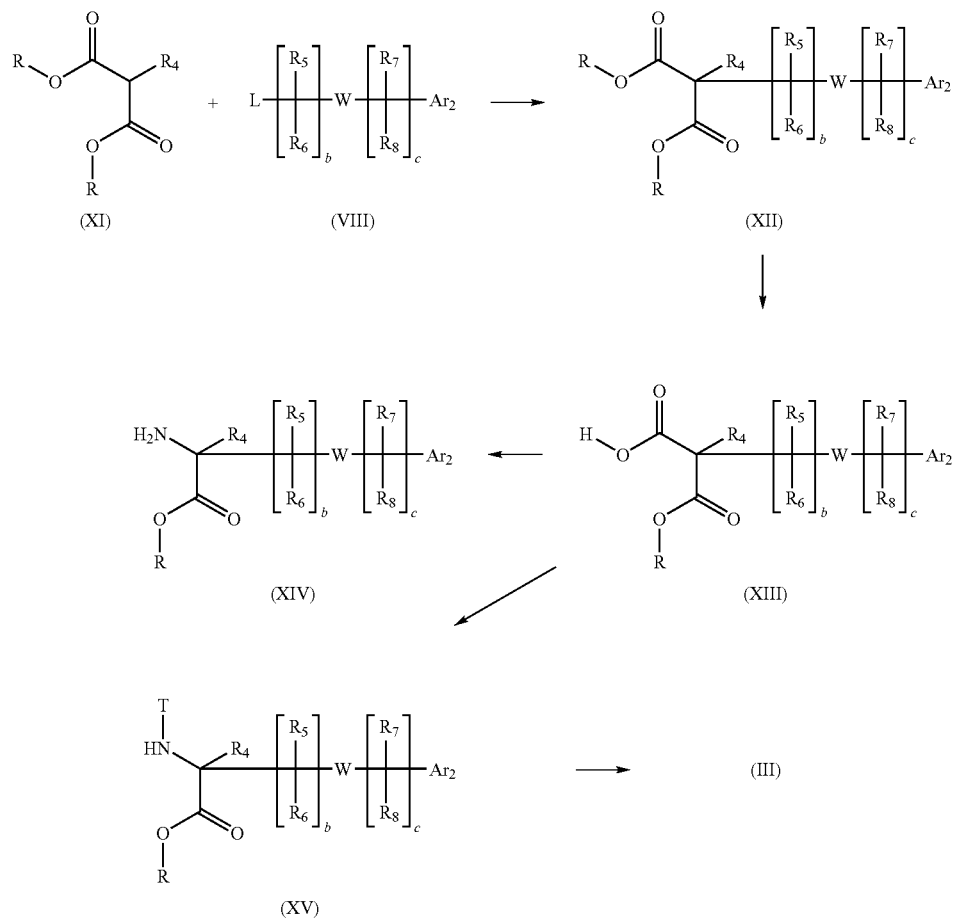

Yet another way to prepare intermediate amino acid derivatives of formula (III) is described in Scheme 6:

Oxiranes of formula XVI where $R_5$, $R_6$ are lower alkyl, in particular $C_1$-$C_5$-alkyl, or hydrogen and $R_4$ is defined as above are in a racemic form prepared by methods described in the general literature. Enantiomerically pure oxiranes of formula XVI are e.g. prepared by methods described by Sharpless (asymmetric Sharpless epoxidation) Transformations to the compounds XVII, XVIII and XIX and the ring opening of the aziridines of formula XXI where W means OH, SH, $NH_2$ are achieved in analogy to procedures described e.g. Castro et al, Tetrahedron Asymmetry 13 (2002) 1321-1325 or e.g. Goodman et al. J. org. Chem. 1995, 60, 790-791 or e.g. Pritchard et al. Tetrahedron, 52 (40), 13035-13050 (1996).

Scheme 6:

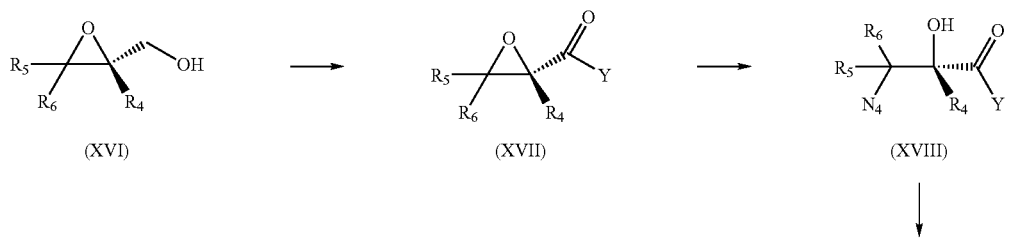

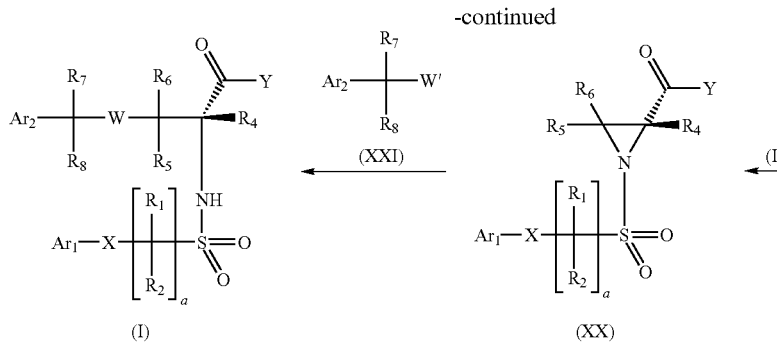
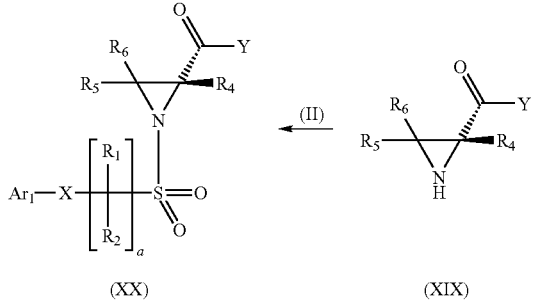

Enantiomeric mixtures of formula I may be separated into the enantiomers by chromatography on chiral stationary phase or by classical methods of fractionated crystallization of diastereomeric salts of a suitable precursor and subsequent conversion into the desired products. Enantiomers or diastereoisomers may also be prepared by enantioselective or diastereoselective synthesis methods.

The compounds of formula I are oils or solids at room temperature and are distinguished by valuable microbicidal properties. They can be used in the agricultural sector or related fields preventatively and curatively in the control of plant-destructive microorganisms. The compounds of formula I according to the invention are distinguished at low rates of concentration not only by outstanding microbicidal, especially fungicidal, activity but also by being especially well tolerated by plants.

Surprisingly, it has now been found that the compounds of formula I have for practical purposes a very advantageous microbiocidal spectrum in the control of phytopathogenic micro-organisms, especially fungi. They possess very advantageous curative and preventive properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. *Cercospora*), Basidiomycetes (e.g. *Puccinia*) and Ascomycetes (e.g. *Erysiphe* and *Venturia*) and especially against Oomycetes (e.g. *Plasmopara*, Peronospora, *Pythium* and *Phytophthora*). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities. Such mixtures are not limited to two active ingredients (one of formula I and one of the list of other fungicides), but to the contrary many comprise more than one active ingredient of the component of formula I and more than one other fungicide. Mixing components which are particularly suited for this purpose include e.g. Azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, S-imazalil, imibenconazole, ipconazole, metconazole, myclobutanil, oxpoconazole, pefurazoate, penconazole, pyrifenox, prochloraz, propiconazole, prothioconazole, simeconazole, tebuconazole, tetraconazole, triadimefon, triadimenol, triflumizole and triticonazole; pyrimidinyl carbinoles, such as ancymidol, fenarimol and nuarimol; 2-amino-pyrimidines, such as bupirimate, dimethirimol and ethirimol; morpholines, such as dodemorph, fenpropidine, fenpropimorph, spiroxamine and tridemorph; anilinopyrimidines, such as cyprodinil, mepanipyrim and pyrimethanil; pyrroles, such as fenpiclonil and fludioxonil; phenylamides, such as benalaxyl, furalaxyl, metalaxyl, R-metalaxyl, ofurace and oxadixyl;

benzimidazoles, such as benomyl, carbendazim, debacarb, fuberidazole and thiabendazole; dicarboximides, such as chlozolinate, dichlozoline, iprodione, myclozoline, procymidone and vinclozoline; carboxamides, such as carboxin, fenfuram, flutolanil, furametpyr, mepronil, oxycarboxin and thifluzamide; guanidines, such as guazatine, dodine and iminoctadine; strobilurines, such as azoxystrobin, dimoxystrobin (SSF-129), fluoxastrobin, kresoxim-methyl, metominostrobin, orysastrobin, picoxystrobin, pyraclostrobin and trifloxystrobin; dithiocarbamates, such as ferbam, mancozeb, maneb, metiram, propineb, thiram, zineb and ziram; N-halomethylthiotetrahydrophthalimides, such as captafol, captan, dichlofluanid, fluoromides, folpet and tolyfluanid; Copper-compounds, such as Bordeaux mixture, copper hydroxide, copper oxychloride, copper sulfate, cuprous oxide, mancopper and oxine-copper; nitrophenol-derivatives, such as dinocap and nitrothal-isopropyl; organo-P-derivatives, such as edifenphos, iprobenphos, isoprothiolane, phosdiphen, pyrazophos and tolclofos-methyl; various others, such as acibenzolar-S-methyl, anilazine, benthiavalicarb, blasticidin-S, boscalid, chinomethionate, chloroneb, chlorothalonil, IKF-916 (proposed name cyazofamid), cyflufenamid, cymoxanil, dichlone, diclomezine, dicloran, diethofencarb, dimethomorph, ethaboxam, fenoxanil, SYP-LI90 (proposed name: flumorph), dithianon, etridiazole, famoxadone, fenamidone, fentin, ferimzone, fluazinam, flusulfamide, fenhexamid, fosetyl-aluminium, hymexazol, iprovalicarb, kasugamycin, methasulfocarb, metrafenone, pencycuron, phthalide, picobenzamid, polyoxins, probenazole, propamocarb, pyroquilon, proquinazid, quinoxyfen, quintozene, silthiofam, sulfur, triazoxide, triadinil, tricyclazole, triforine, validamycin, or zoxamide.

In the above mentioned mixtures, the mixture ratio of the active ingredients is so selected that it reaches optional control of the phytopathogenic microorganism on the host plants. This ratio is in general between 100:1 and 1:100, more preferably between 10:1 and 1:10 of a compound of formula I vis-à-vis the second fungicide. The mixtures may not only comprise one of the listed combinational active ingredients, but may comprise more than one additional active ingredients selected from that specified group, thus forming for example 3-way- or even 4-way-mixtures.

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 5.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius. The compounds are numbered with the compound number of the table given below.

PREPARATION EXAMPLES

Example P1

2-Methyl-2-phenylmethanesulfonylamino-3-(4-[1,2,4]triazol-1-yl-phenoxy)-propionic Acid (Tab. 100)

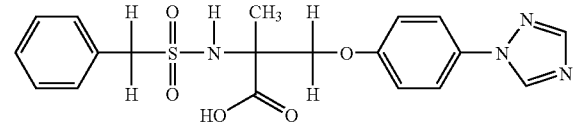

15.9 g 2-[(4-[1,2,4]triazol-1-yl-phenoxy)-methyl]-2-benzylsulfonylamino-butyronitrile are added to 100 ml conc. hydrogen chloride solution with stirring. The suspension is heated to +80° C. for 4 hours, cooled to room temperature the formed solid is filtered off and thoroughly washed with water and re-crystallized from i-propanol. Yield 9.83 g white crystals. M.p. 148-151° C.

Example P2

2-Methyl-2-phenylmethanesulfonylamino-3-(4-[1,2,4]triazol-1-yl-phenoxy)-propionamide (Tab.: 101)

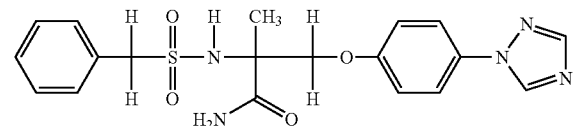

1.98 g 2-[(4-[1,2,4]Triazol-1-yl-phenoxy)-methyl]-2-benzylsulfonylamino-butyronitrile, 1.3 g potassium hydroxide, 4 drops of hydro-peroxide (30%) in 10 ml water are stirred for 18 hours at room temperature. After addition of 60 ml water the solution is acidified to pH 2 by addition of a 2 N hydrogen chloride solution and extracted with ethyl acetate. After evaporation of the solvent the residue is subjected to flash chromatography (eluant: ethyl acetate) to give 0.160 g of the product as white crystals. M.p. 195-198° C.

Example P3

3-(4-Ethoxy-phenoxy)-2-methyl-2-phenylmethane-sulfonylamino-propionic Acid Methyl Ester. (Tab.: 082)

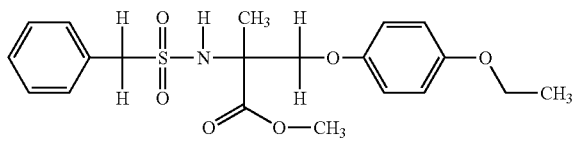

a) 1-Ethoxy-4-methylsulfanylmethoxy-benzene 45.0 g of 4-ethoxyphenol is added to a solution of 40.2 g of potassium t-butylate in 500 ml of tetrahydrofurane and stirred for 10 minutes. The solvent is thoroughly evaporated on the rotavap and the residue dissolved in 200 ml dimethylformamide. 40.9 g of chloromethyl-methylsulfide are added drop wise over 1 h letting the reaction mixture warm up to +41° C. Stirring is continued for 3.5 hours at room temperature. The reaction mixture is poured into water and extracted with ethyl acetate, washed with brine and water, dried over sodium sulfate and the solvent evaporated. Flash chromatography (eluant: hexane/ethyl acetate 98:2) yielded 36.3 g of yellow oil.

b) 1-Chlormethoxy-4-ethoxy-benzene 38 g of 1-ethoxy-4-methylsulfanylmethoxy-benzene are dissolved in 300 ml of dichloromethane and 26.2 g of sulfuryl chloride are added slowly (slightly exothermic). After 2 hours of stirring at room temperature the solvent is evaporated thoroughly to yield 36.2 of yellow-brown oil, which is used in the following reaction without further purification.

c) 2-(4-Ethoxy-phenoxy-methyl)-2-methyl-malonic Acid Dimethyl Ester 11.5 g of sodium hydride (55% in oil) are suspended in 150 ml of tetrahydrofurane under nitrogen atmosphere. 29.6 g of methyl-malonic acid dimethyl ester are added during 20 minutes while maintaining the temperature at +25° C. by cooling. Stirring is continued until the gas evolution ceased. 37.8 g of 1-Chlormethoxy-4-ethoxy-benzene are then added over a period of 20 minutes maintaining the temperature at around +30° C. After 1.5 hours the mixture is cooled to +5° C. and 25 ml of ammonium chloride is added carefully, then poured into water and extracted with ethyl acetate. The organic phase is washed with brine and dried over sodium sulfate, filtered and the solvent evaporated. Flash chromatography (eluant: hexane/ethyl acetate 95:5) yielded 41.6 g of a slightly yellow powder.

d) 2-(4-Ethoxy-phenoxy-methyl)-2-methyl-malonic Acid Mono Methyl Ester 36.4 g of 2-(4-Ethoxy-phenoxy)-2-methyl-malonic acid dimethyl ester are dissolved in 450 ml methanol. A solution of 8.9 g potassium hydroxide pellets dissolved in 30 ml of water is added over a period of 20 minutes and stirring is continued for 20 hours at room temperature. Methanol is evaporated under reduced pressure and the residue dissolved in water and neutral residues extracted with t-butyl-methyl ether. The water phase is acidified to pH 3 and extracted with ethyl acetate, the organic extract washed with brine and dried over sodium sulfate. Evaporation of the solvent yielded 33.4 g of a slightly yellow powder pure enough for further reactions.

e) N-t-butoxycarbonyl-3-(4-ethoxy-phenoxy)-2-methyl-propionic Acid Methyl Ester 32.8 g of 2-(4-Ethoxy-phenoxy)-2-methyl-malonic acid mono methyl ester are dissolved in dry toluene by slight warming followed by the addition of 12.9 g of triethylamine and 41.6 g diphenylphosphoryl azide (DPPA). The mixture is slowly heated to reflux. A vigorous evolution of gas started at a temperature of about +75° C. After 2.5 hours refluxing 80 ml of dry t-butanol is slowly added and refluxing continued for 12 hours. The solvents of the reaction mixture are evaporated and the residue extracted with ethyl acetate. The organic phase is washed with citric acid solution (5%), saturated potassium carbonate solution and brine, dried over sodium sulfate and evaporated to yield after flash chromatography (eluant: hexane/ethyl acetate 9:1) 14.8 g of a slightly yellow oil.

f) 2-Amino-3-(4-ethoxy-phenoxy)-2-methyl-propionic Acid Methyl Ester 0.57 g N-t-Butoxycarbonyl-3-(4-ethoxy-phenoxy)-2-methyl-propionic acid methyl ester are dissolved in 20 ml 1 N trifluoroacetic acid in dichloromethane. After 3.5 hours at room temperature the solvents are evaporated to yield 0.41 g product.

g) 0.340 g 2-amino-3-(4-ethoxy-phenoxy)-2-methyl-propionic acid methyl ester are dissolved in 10 ml tetrahydrofurane followed by the addition of 0.310 g of 1,4-diazabicyclo[2,2,2]α-tane DABCO and 0.310 g of phenyl-methansulfochloride. After stirring for 20 hours at room temperature the mixture was without further work-up procedure subjected to flash chromatography (eluant: hexane/ethyl acetate 3:1) to give 0.301 g 3-(4-ethoxy-phenoxy)-2-methyl-2-phenyl-methanesulfonylamino-propionic acid methyl ester as resinous oil.

Example P4

3-(4-Ethoxy-phenoxy)-N-methoxy-2,N-dimethyl-2-phenylmethanesulfonylamino-propionamide (Tab.: 083)

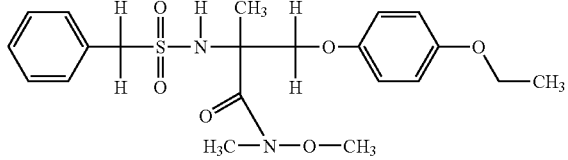

a) 14.8 g N-t-Butoxycarbonyl-3-(4-ethoxy-phenoxy)-2-methyl-propionic acid methyl ester are dissolved in 200 ml methanol and a solution of 5.5 g potassium hydroxide pellets dissolved in 10 ml of water added to it. After heating to reflux for 20 hours the solvents are evaporated, the residue treated with water and neutral organic matter removed by extraction with t-butyl-methylether The water phase is made acidic by addition of 2N hydrogen chloride solution and extracted with ethyl acetate. The ethyl acetate solution is washed with brine, dried over sodium sulfate, filtered and evaporated to yield 13.5 g N-t-butoxycarbonyl-3-(4-ethoxy-phenoxy)-2-methyl-propionic acid as a slightly brown resinous product which is used for further reactions without purification.

b) 1.0 g of N-t-Butoxycarbonyl-3-(4-ethoxy-phenoxy)-2-methyl-propionic acid, 0.316 g methoxy-methylamine hydrochloride and 0.960 g tri-ethylamine are mixed in 20 ml dichloromethane. After addition of 0.825 g bis-(2-oxo-3-oxazolidinyl)phosphinic acid chloride (BOPP—Cl) the mixture is stirred for 18 hours at room temperature. The solvent is then evaporated and the residue, without further work-up procedure, subjected to flash to give 0.190 g N-t-butoxycarbonyl-3-(4-ethoxy-phenoxy)-2-methyl-N-methyl-N-methoxy-propionamide.

c) 0.180 g N-t-Butoxycarbonyl-3-(4-ethoxy-phenoxy)-2-methyl-N-methyl-N-methoxy-propionamide dissolved in 6 ml of 1 N trifluoro-acetic acid in dichloromethane are stirred at room temperature for 20 hours. The solvent is evaporated, water added and made basic to pH 8 by addition of 2 N sodium hydroxide. After extraction with ethyl acetate, washing of the organic phase with brine and drying it over sodium sulfate 0.100 g of 3-(4-ethoxy-phenoxy)-2-methyl-N-methyl-N-methoxy-propionamide are recovered and used in the next step without further purification.

d) 0.100 g 3-(4-ethoxy-phenoxy)-2-methyl-N-methyl-N-methoxy-propionamide and 0.081 g DABCO are dissolved in 8 ml tetrahydrofurane. After addition of 0.081 phenyl-methansulfochlorid the mixture is stirred for 20 hours at room temperature. This mixture is then subjected to flash chromatography without further work-up to yield 45 mg of a white solid. M.p. 179-181° C.

Example P5

3-(4-Ethoxy-phenoxy)-2-methyl-2-phenylmethane-sulfonylamino-1-morpholin-4-yl-propan-1-one (Tab.: 092)

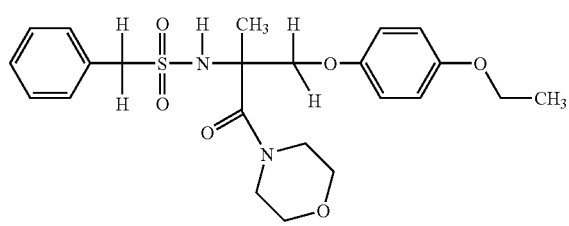

0.370 g 2-Amino-3-(4-ethoxy-phenoxy)-2methyl-1-morpholin-4-yl-propan-1-one and 0.276 g DABCO are dissolved in 8 ml tetrahydrofurane. After addition of 0.274 phenyl-methane sulfonyl chloride the mixture is stirred for 20 h at room temperature. This mixture is then subjected to flash chromatography without further work-up to yield 260 mg of a white solid. M.p. 109-111° C.

Example P6

3-(4-Ethoxy-phenoxy)-2-methyl-2-phenylmethane-sulfonylamino-N-prop-2-ynyl-propionamide (Tab.: 087)

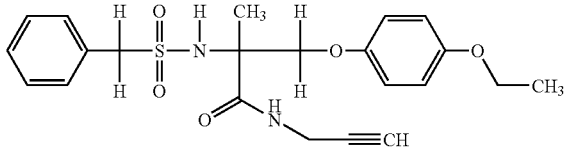

0.880 g 2-Amino-3-(4-ethoxy-phenoxy)-2methyl-N-prop-2-ynyl-propionamide and 0.233 g DABCO are dissolved in 8 ml tetrahydrofurane. After addition of 0.232 phenyl-methansulfonyl chloride the mixture is stirred for 20 hours. This mixture is then subjected to flash chromatography without further work-up to yield 320 mg of a white solid. M.p. 155-156° C.

Example P7

(+)-3-(4-Chloro-phenoxy)-2-methyl-2-phenyl-methanesulfonylamino-propionamide

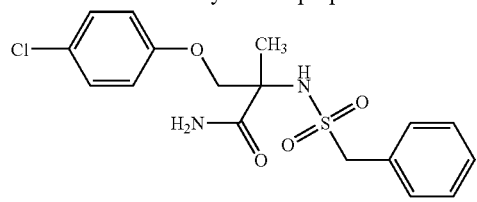

a) (+)-2-(4-chlor-phenoxy-methyl)-2-methyl-malonic Acid Mono Methyl Ester

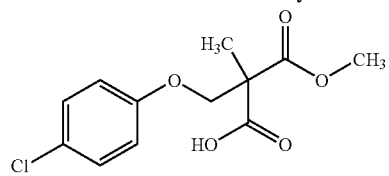

300 ml Phosphate buffer are heated to 30° C. and 124 mg of pig liver esterase are added and left for 15 minutes 3 g of 2-(4-chlor-phenoxy-methyl)-2-methyl-malonic acid dimethyl ester in 10 ml of isopropanol the mixture is stirred at +30° C. for 17 hours. The reaction mixture is extracted with ethylacetate to remove neutral organic matter, the remaining solution acidified to pH 2 with 2N hydrogenchlorid and extracted again with ethylacetate. The organic extract is dried over sodium sulfate, the solvent evaporated and the residue chromatographed (RP-18 column, eluant: acetonitril/water 1:1). Yield 1.73 g, M.p. 93° C.

$[\alpha]=+6.9°$ (c=0.0109 g ml$^{-1}$ acetonitrile).

b) (−)—N-t-butoxycarbonyl-3-(4-chloro-phenoxy)-2-methyl-propionic acid methyl ester is prepared as described above. $[\alpha]=-93.7°$ (c=0.0099 g ml$^{-1}$ acetonitrile).

c) (−)—N-t-butoxycarbonyl-3-(4-chloro-phenoxy)-2-methyl-propionic acid amide $[\alpha]=-3.7°$ (c=0.0111 g ml$^{-1}$ acetonitrile).

d) (+)-3-(4-Chloro-phenoxy)-2-methyl-2-phenylmethane-sulfonylamino-propionamide, $[\alpha]=+9.4°$ (c=0.0101 g ml$^{-1}$ dimethylsulfoxide)

In analogous manner the compounds of following Table 1 are obtained.

TABLE

| No. | $R_1$ | $R_2$ | $R_3$ | $R_4$ | $R_5$ | $R_6$ | $(R_{15})_n$ | $(R_{20})_n$ | $R_{21}$ | Y | m.p. [°C] |
|---|---|---|---|---|---|---|---|---|---|---|---|
| 001 | H | H | H | $CH_3$ | H | H | H | 2-Cl | H | OH | |
| 002 | H | H | H | $CH_2CH_3$ | H | H | H | 2-Cl | H | OH | |
| 003 | H | H | H | $CH_2CH_3$ | H | H | H | 2-Cl | H | $NH_2$ | |
| 004 | H | H | H | $CH_3$ | H | H | H | 2-Cl | H | $NH_2$ | |
| 005 | H | H | H | $CH_2CH_3$ | H | H | H | 2-Cl | H | $NHCH_3$ | |
| 006 | H | H | H | $CH_3$ | H | H | H | 2-Cl | H | $NHCH_3$ | |
| 007 | H | H | H | $CH_2CH_3$ | H | H | H | 2-Cl | H | $N(CH_3)_2$ | |
| 008 | H | H | H | $CH_3$ | H | H | H | 2-Cl | H | $OCH_3$ | |
| 009 | H | H | H | $CH_2CH_3$ | H | H | H | 2-Cl | H | $OCH_2CH_3$ | |
| 010 | H | H | H | $CH_3$ | H | H | H | 2-Cl | H | morpholino | |
| 011 | H | H | H | $CH_3$ | H | H | H | 2-Cl | H | $OCH_3$ | |
| 012 | H | H | H | $CH_2CH_3$ | H | H | H | 2,3-$Cl_2$ | H | OH | |
| 013 | H | H | H | $CH_3$ | H | H | H | 2,3-$Cl_2$ | H | OH | |
| 014 | H | H | H | $CH_2CH_3$ | H | H | H | 3,4-$Cl_2$ | H | OH | |
| 015 | H | H | H | $CH_3$ | H | H | H | 2,4-$Cl_2$ | H | OH | |
| 016 | H | H | H | $CH_2CH_3$ | H | H | H | 4-$CF_3$ | H | OH | |
| 017 | H | H | H | $CH_3$ | H | H | H | 4-$CF_3$ | H | OH | |
| 018 | H | H | H | $CH_2CH_3$ | H | H | H | 2,3-$Cl_2$ | H | $OCH_3$ | |
| 019 | H | H | H | $CH_3$ | H | H | H | 2,3-$Cl_2$ | H | $OCH_3$ | |
| 020 | H | H | H | $CH_2CH_3$ | H | H | H | 3,4-$Cl_2$ | H | $OCH_3$ | |
| 021 | H | H | H | $CH_3$ | H | H | H | 2,4-$Cl_2$ | H | $OCH_3$ | |
| 022 | H | H | H | $CH_2CH_3$ | H | H | H | 4-$CF_3$ | H | $OCH_3$ | |
| 023 | H | H | H | $CH_3$ | H | H | H | 4-$CF_3$ | H | $OCH_3$ | |
| 024 | H | H | H | $CH_2CH_3$ | H | H | H | 2,3-$Cl_2$ | H | $NHCH_3$ | |
| 025 | H | H | H | $CH_3$ | H | H | H | 2,3-$Cl_2$ | H | $NHCH_3$ | |
| 026 | H | H | H | $CH_2CH_3$ | H | H | H | 3,4-$Cl_2$ | H | $NHCH_3$ | |
| 027 | H | H | H | $CH_3$ | H | H | H | 2,4-$Cl_2$ | H | $NHCH_3$ | |
| 028 | H | H | H | $CH_2CH_3$ | H | H | H | 4-$CF_3$ | H | $NHCH_3$ | |
| 029 | H | H | H | $CH_3$ | H | H | H | 4-$CF_3$ | H | $OCH_3$ | |
| 030 | H | H | H | $CH_2CH_3$ | H | H | H | 4-$CH(CH_3)_2$ | H | $OCH_3$ | |
| 031 | H | H | H | $CH_3$ | H | H | H | 4-Cl | H | $OCH_3$ | |
| 032 | H | H | H | $CH_2CH_3$ | H | H | 4-Cl | 4-Cl | H | $OCH_3$ | |
| 033 | H | H | $CH_3$ | $CH_3$ | H | H | H | 4-Cl | H | $OCH_3$ | |
| 034 | H | H | H | $CH_2CH_3$ | H | H | H | 4-Cl | H | $OCH_3$ | |
| 035 | H | H | H | $CH_2CH_3$ | $CH_3$ | $CH_2CH_3$ | H | 4-Cl | H | $OCH_3$ | |
| 036 | H | H | H | $CH_3$ | $CH_3$ | $CH_3$ | H | 4-Cl | H | $OCH_3$ | |
| 037 | H | H | H | $CH_2CH_3$ | $CH_3$ | H | H | 4-Cl | H | $NHCH_3$ | |
| 038 | H | H | H | $CH_2CH_3$ | H | H | H | 4-Cl | H | $NHCH_3$ | |
| 039 | H | H | H | $CH_3$ | H | H | H | 3-$OCH_3$, 4-Cl | H | OH | |
| 040 | H | H | H | $CH_2CH_3$ | H | H | H | 4-$OCF_3$ | H | $OCH_3$ | |
| 041 | H | H | H | $CH_3$ | H | H | H | 4-$OCF_3$ | H | $OCH_3$ | |
| 042 | H | H | H | $CH_3$ | H | H | 4-F | 4-F | H | $OCH_3$ | |
| 043 | $CH_3$ | H | H | $CH_3$ | H | H | 4-F | 4-F | H | $NHCH_3$ | |

TABLE-continued

| No. | R₁ | R₂ | R₃ | R₄ | R₅ | R₆ | (R₁₅)ₙ | (R₂₀)ₙ | R₂₁ | Y | m.p. [°C] |
|---|---|---|---|---|---|---|---|---|---|---|---|
| 044 | H | H | H | CH₂CH₃ | H | H | H | 4-F | H | NHCH₃ | |
| 045 | H | H | H | CH₃ | H | H | H | 4-CH₃ | H | OCH₃ | |
| 046 | H | H | H | CH₂CH₃ | H | H | 4-F | 4-CH₃ | H | OCH₃ | |
| 047 | H | H | H | CH₃ | H | H | H | 4-CH₃ | H | NHCH₃ | |
| 048 | H | H | H | CH₂CH₃ | H | H | H | 3-CH₃ | H | OH | |
| 049 | H | H | H | CH₃ | H | H | H | 4-OCH₃ | H | OCH₃ | |
| 050 | H | H | H | CH₂CH₃ | H | H | H | 4-OCH₃ | H | OCH₃ | |
| 051 | H | H | H | CH₂CH₃ | CH₃ | CH₃ | H | 4-OCH₃ | H | NHCH₃ | |
| 052 | H | H | H | CH₃ | CH₃ | CH₃ | H | 4-OCH₃ | H | OH | |
| 053 | H | H | H | CH₂CH₃ | CH₃ | CH₂CH₃ | H | 4-OCH₃ | H | OH | |
| 054 | H | H | H | CH₂CH₃ | H | H | H | 3-Cl; 4-OCH₃ | H | OCH₃ | |
| 055 | H | H | H | CH₃ | H | H | H | 3-Cl; 4-OCH₃ | H | OCH₃ | |
| 056 | H | H | H | CH₂CH₃ | H | H | H | 2-F; 4-OCH₃ | H | OCH₃ | |
| 057 | H | H | H | CH₃ | H | H | H | 2-Cl; 4-OCH₃ | H | OCH₃ | |
| 058 | H | H | H | CH₃ | H | H | H | H | 3-methyl-1,2,4-thiadiazol-5-yloxy (4) | OCH₃ | |
| 059 | H | H | CH₂—OCH₂CH₃ | CH₂CH₃ | H | H | H | H | 3-methyl-1,2,4-thiadiazol-5-yloxy (4) | OCH₃ | |
| 060 | H | H | H | CH₃ | H | H | H | H | 1H-pyrazol-1-yl (4) | OCH₃ | |
| 061 | H | H | H | CH₂CH₃ | H | H | 4-F | H | 1H-pyrazol-1-yl (4) | OCH₃ | |
| 062 | CH₃ | H | H | CH₃ | H | H | H | H | 1H-pyrazol-1-yl (4) | NHCH₃ | |
| 063 | CH₃ | CH₃ | H | CH₂CH₃ | H | H | H | H | 1H-pyrazol-1-yl (4) | OCH₃ | |

TABLE-continued

| No. | R$_1$ | R$_2$ | R$_3$ | R$_4$ | R$_5$ | R$_6$ | (R$_{15}$)$_n$ | (R$_{20}$)$_n$ | R$_{21}$ | Y | m.p. [° C.] |
|---|---|---|---|---|---|---|---|---|---|---|---|
| 064 | H | H | H | CH$_3$ | H | H | H | H | (2-methoxypyridin-yl)(4) | OH | |
| 065 | H | H | H | CH$_2$CH$_3$ | H | H | H | H | 4-CONH$_2$ | OCH$_3$ | |
| 066 | H | H | H | CH$_2$CH$_3$ | H | H | H | H | 4-CONH$_2$ | NHCH$_3$ | |
| 067 | H | H | H | CH$_3$ | H | H | H | H | (3,5-dichloro-2-methoxypyridinyl)(4) | OCH$_3$ | |
| 068 | H | H | H | CH$_3$ | H | H | 4-F | 4-SCH$_3$ | H | OH | |
| 069 | H | H | H | CH$_2$CH$_3$ | H | H | H | 4-SCH$_3$ | H | OH | |
| 070 | H | H | H | CH$_3$ | H | H | H | 4-SO$_2$CH$_3$ | H | OCH$_3$ | |
| 071 | H | H | H | CH$_2$CH$_3$ | H | H | H | 4-CN | H | OH | |
| 072 | H | H | H | CH$_3$ | H | H | H | 4-CN | H | OH | |
| 073 | H | H | H | (CH$_2$)$_2$CH$_3$ | H | H | H | 4-CN | H | OH | |
| 074 | H | H | H | CH$_2$(CH$_3$)$_2$ | H | H | H | 4-CN | H | OH | |
| 075 | H | H | H | CH$_3$ | H | H | H | H | (oxazolyl)(4) | OCH$_3$ | |
| 076 | H | H | H | CH$_2$CH$_3$ | H | H | H | H | (oxazolyl)(4) | OCH$_3$ | |
| 077 | H | H | H | CH$_2$CH$_3$ | H | H | H | 4-OCH$_2$CH$_3$ | H | OH | foam |
| 078 | H | H | H | CH$_3$ | H | H | H | 4-OCH$_2$CH$_3$ | H | NH—CH(CH$_3$)-phenyl | 179–181 |
| 079 | H | H | H | CH$_3$ | H | H | H | 4-OCH$_2$CH$_3$ | H | N(CH$_3$)OCH$_3$ | 111 |
| 080 | H | H | H | CH$_3$ | H | H | H | 4-OCH$_2$CH$_3$ | H | NH(CH$_2$)$_2$-3,4-dimethoxy-phenyl | 156–157 |
| 081 | H | H | H | CH$_3$ | H | H | H | 4-OCH$_2$CH$_3$ | H | N(CH$_3$)$_2$ | resinous oil |
| 082 | H | H | H | CH$_3$ | H | H | H | 4-OCH$_2$CH$_3$ | H | OCH$_3$ | oil |
| 083 | H | H | H | CH$_3$ | H | H | H | 4-OCH$_2$CH$_3$ | H | NH$_2$ | solid |

| No. | R₁ | R₂ | R₃ | R₄ | R₅ | R₆ | (R₁₅)n | (R₂₀)n | R₂₁ | Y | m.p. [° C.] |
|---|---|---|---|---|---|---|---|---|---|---|---|
| 084 | H | H | H | CH₂CH₃ | H | H | 4-F | 4-OCH₂CH₃ | H | OCH₃ | 155–156 |
| 085 | H | H | H | CH₂CH₃ | H | H | 4-F | 4-OCH₂CH₃ | H | NHCH₃ | solid |
| 086 | CH₃ | H | H | CH₂CH₃ | H | H | 4-F | 4-OCH₂CH₃ | H | OH | |
| 087 | H | H | H | CH₃ | H | H | H | 4-OCH₂CH₃ | H | NH-propargyl | 130–131 |
| 088 | H | H | H | CH₃ | H | H | H | 4-OCH₂CH₃ | H | NHCH₃ | |
| 089 | H | H | H | CH₃ | H | H | H | 4-OCH₂CH₃ | H | OCH₂CH₃ | |
| 090 | H | H | H | CH₃ | H | H | H | 4-OCH₂CH₃ | H | OCH(CH₃)₂ | 109–111 |
| 091 | H | H | H | CH₃ | H | H | H | 4-OCH₂CH₃ | H | NHCH₂-4-methoxy-phenyl | |
| 092 | H | H | H | CH₃ | H | H | H | 4-OCH₂CH₃ | H | morpholino | |
| 093 | CH₃ | H | H | CH₃ | H | H | 4-F | 4-OCH₂CH₃ | H | OH | |
| 094 | H | H | H | CH₂CH₃ | H | H | 4-Cl | 4-OCH₂CH₃ | H | OCH₃ | |
| 095 | H | H | H | CH₃ | H | H | 4-Cl | 4-OCH₂CH₃ | H | NHCH₃ | |
| 096 | H | H | H | CH₂CH₃ | H | H | 2-F | 4-OCH₂CH₃ | H | OCH₃ | |
| 097 | H | H | H | CH₃ | H | H | 2-F | 4-OCH₂CH₃ | H | NHCH₃ | |
| 098 | H | H | H | (CH₂)₂CH₃ | H | H | H | 4-OCH₂CH₃ | H | OCH₃ | |
| 099 | H | H | H | CH₂CH₃ | H | H | H | H | imidazol-1-yl (4) | OCH₃ | — |
| 100 | H | H | H | CH₃ | H | H | H | H | imidazol-1-yl (4) | OH | 148–151 |
| 101 | H | H | H | CH₃ | H | H | H | H | imidazol-1-yl (4) | NH₂ | 195–198 |
| 102 | H | H | H | CH₃ | H | H | H | H | imidazol-1-yl (4) | NHCH₃ | 176–181 |
| 103 | H | H | H | CH₃ | H | H | H | H | imidazol-1-yl (4) | OCH₃ | solid |

TABLE-continued

| No. | R₁ | R₂ | R₃ | R₄ | R₅ | R₆ | (R₁₅)ₙ | Y | (R₂₀)ₙ | R₂₁ | Y | m.p. [° C.] |
|---|---|---|---|---|---|---|---|---|---|---|---|---|
| 104 | H | H | H | CH₃ | H | H | H | H | imidazol-1-yl (4) | —NH-4-Cl-phenyl | resin |
| 105 | H | H | H | CH₃ | H | H | H | H | imidazol-1-yl (4) | O-4-Cl-phenyl | |
| 106 | H | H | H | CH₂CH₃ | H | H | 4-F | H | imidazol-1-yl (4) | OH | resin |
| 107 | H | H | H | CH₃ | H | H | H | H | imidazol-1-yl (4) | NH(CH₂)₂-3,4-dimethoxy-phenyl | |
| 108 | H | H | H | CH₃ | H | H | H | 2-Cl | imidazol-1-yl (4) | NH—CH(CH₃)-phenyl | resin |
| 109 | H | H | H | CH₃ | H | H | H | 2-Cl | imidazol-1-yl (4) | NH-propargyl | resin |
| 110 | H | H | H | CH₃ | H | H | H | H | imidazol-1-yl (4) | morpholino | |
| 111 | H | H | H | CH₃ | H | H | H | H | imidazol-1-yl (4) | N(CH₃)₂ | |
| 112 | H | H | H | CH₃ | H | H | H | H | imidazol-1-yl (4) | OCH₂CH₃ | |

TABLE-continued

| No. | R₁ | R₂ | R₃ | R₄ | R₅ | R₆ | (R₁₅)ₙ | (R₂₀)ₙ | R₂₁ | Y | m.p. [° C.] |
|---|---|---|---|---|---|---|---|---|---|---|---|
| 113 | H | H | H | CH₃ | H | H | H | H | imidazol-1-yl (4) | OCH(CH₃)₂ | |
| 114 | H | H | H | CH₃ | H | H | H | H | imidazol-1-yl (4) | NHCH₂CH₃ | |
| 115 | H | H | H | CH₃ | H | H | H | H | imidazol-1-yl (4) | NHOCH₃ | resin |
| 116 | H | H | H | CH₃ | H | H | H | H | imidazol-1-yl (4) | NH-n-butyl | |
| 117 | H | H | H | (CH₂)₂CH₃ | H | H | H | H | imidazol-1-yl (4) | OCH₃ | |
| 118 | H | H | H | CH₂(CH₃)₂ | H | H | H | H | imidazol-1-yl (4) | NHCH₃ | |
| 119 | H | H | H | CH₂F | H | H | H | H | imidazol-1-yl (4) | OH | |
| 120 | H | H | H | CH₃ | H | H | H | H | 3,5-dimethylpyrazol-1-yl (4) | OCH₃ | |

TABLE-continued

| No. | R1 | R2 | R3 | R4 | R5 | R6 | (R15)n | (R20)n | R21 | Y | m.p. [°C] |
|---|---|---|---|---|---|---|---|---|---|---|---|
| 121 | H | H | H | CH3 | H | H | H | H | 3,5-dimethyl-pyrazol-1-yl (4) | NHCH3 | |
| 122 | H | H | H | CH2CH3 | H | H | H | H | 3,5-dimethyl-pyrazol-1-yl (4) | OH | |
| 123 | H | H | H | CH3 | H | H | H | H | 3,5-dimethyl-pyrazol-1-yl (4) | OH | |
| 124 | H | H | H | CH2CH3 | H | H | H | H | pyridin-2-yl (4) | NHCH3 | |
| 125 | H | H | H | CH2CH3 | H | H | H | H | pyridin-2-yl (4) | OH | |
| 126 | H | H | H | CH2CH3 | H | H | H | H | 2-methyl-thiazol-4-yl (4) | OH | |
| 127 | H | H | H | CH3 | H | H | H | H | 2-methyl-thiazol-4-yl (4) | OH | |

TABLE-continued

| No. | R₁ | R₂ | R₃ | R₄ | R₅ | R₆ | (R₁₅)ₙ | (R₂₀)ₙ | R₂₁ | Y | m.p. [° C.] |
|---|---|---|---|---|---|---|---|---|---|---|---|
| 128 | H | H | H | CH₂CH₃ | H | H | H | H | (4) pyrazolyl | OH | |
| 129 | H | H | H | CH₃ | H | H | H | H | (4) pyrazolyl | OCH₃ | |
| 130 | H | H | H | CH₃ | H | H | H | H | (4) pyrazolyl | NHCH₃ | |
| 131 | H | H | H | CH₃ | H | H | H | H | (4) pyrazolyl | OH | |
| 132 | H | H | H | CH₂CH₃ | H | H | H | 4-OH | H | NHCH₃ | |
| 133 | H | H | H | CH₂CH₃ | H | H | H | 4-OH | H | NHCH₃ | |
| 134 | H | H | H | CH₂CH₃ | H | H | H | 4-I | H | OH | |
| 135 | H | H | H | CH₃ | H | H | H | 4-I | H | OH | |
| 136 | H | H | H | CH₃ | H | H | H | 4-I | H | OCH₃ | |
| 137 | H | H | H | CH₃ | H | H | 4-F | 4-I | H | NHCH₃ | |
| 138 | H | H | H | CH₂CH₃ | H | H | H | 4-Br | H | OH | |
| 139 | H | H | H | CH₃ | H | H | H | 4-Br | H | OH | |
| 140 | H | H | H | CH₃ | H | H | 4-F | 4-Br | H | NHCH₃ | |
| 141 | H | H | H | CH₃ | H | H | H | H | H | OH | |
| 142 | H | H | H | CH₂CH₃ | H | H | H | H | 4-COCH₂CH₃ | OH | |
| 143 | H | H | H | CH₃ | H | H | H | H | 4-COCH₂CH₃ | OH | |
| 144 | H | H | H | CH₂CH₃ | H | H | H | H | (4) pyrimidinyl | OH | solid |
| 145 | H | H | H | CH₃ | H | H | 4-F | H | (4) pyrimidinyl | OH | |

TABLE-continued

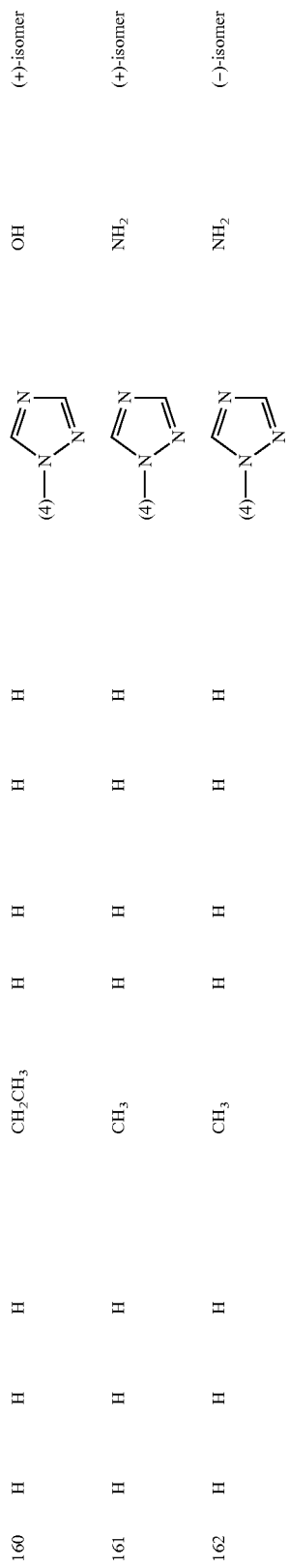

| No. | R1 | R2 | R3 | R4 | R5 | R6 | (R15)n | (R20)n | R21 | Y | m.p. [° C.] |
|---|---|---|---|---|---|---|---|---|---|---|---|
| 146 | CH3 | H | H | CH3 | H | H | H | H | (4) pyrimidine | OH | |
| 147 | H | H | H | CH3 | H | H | H | H | (4) pyrimidine | NHCH3 | |
| 148 | H | H | H | CH2CH3 | H | H | H | H | 4-COCH3 | OH | |
| 149 | H | H | H | CH3 | H | H | H | H | 4-COCH3 | OH | |
| 150 | H | H | H | CH2CH3 | H | H | 4-F | H | 4-COCH3 | OH | |
| 151 | H | H | H | CH3 | H | H | H | 3,4-(OCH3)2 | H | OH | |
| 152 | H | H | H | CH2CH3 | H | H | 4-F | 3,4-(OCH3)2 | H | OH | |
| 153 | H | H | H | CH2CH3 | H | H | H | 4-OCH2C≡CH | H | OH | |
| 154 | H | H | H | CH2CH2CH3 | H | H | H | 4-OCH2C≡CH | H | OH | |
| 155 | H | H | H | CH3 | H | H | H | 4-OCH2CH=CH2 | H | OH | |
| 156 | H | H | H | CH2CH3 | H | H | H | 4-OCH2CH=CH2 | H | OH | |
| 157 | H | H | H | CH2CH2CH3 | H | H | H | 4-OCH2CH=CH2 | H | OH | |
| 158 | H | H | H | CH2CH3 | H | H | H | H | (4) imidazole | OH | (−)-isomer |
| 159 | H | H | H | CH2CH3 | H | H | H | H | (4) imidazole | OH | (+)-isomer |
| 160 | H | H | H | CH3 | H | H | H | H | (4) imidazole | NH2 | (+)-isomer |
| 161 | H | H | H | CH3 | H | H | H | H | (4) imidazole | NH2 | (−)-isomer |
| 162 | H | H | H | CH3 | H | H | H | H | (4) imidazole | NH2 | (−)-isomer |

TABLE-continued

| No. | R$_1$ | R$_2$ | R$_3$ | R$_4$ | R$_5$ | R$_6$ | (R$_{15}$)$_n$ | (R$_{20}$)$_n$ | R$_{21}$ | Y | m.p. [° C.] |
|---|---|---|---|---|---|---|---|---|---|---|---|
| 163 | H | H | H | CH$_3$ | H | H | H | H | (4)- imidazolyl | OH | (+)-isomer |
| 164 | H | H | H | CH$_3$ | H | H | H | H | (4)- imidazolyl | OH | (−)-isomer |
| 165 | H | H | H | CH$_2$CH$_3$ | H | H | H | 4-OCH$_2$CH$_3$ | H | OH | (−)-isomer |
| 166 | H | H | H | CH$_2$CH$_3$ | H | H | H | 4-OCH$_2$CH$_3$ | H | OH | (+)-isomer |
| 167 | H | H | H | CH$_3$ | H | H | H | 4-OCH$_2$CH$_3$ | H | OH | (−)-isomer |
| 168 | H | H | H | CH$_3$ | H | H | H | 4-OCH$_2$CH$_3$ | H | NH$_2$ | (−)-isomer |
| 169 | H | H | H | CH$_3$ | H | H | H | 4-OCH$_2$CH$_3$ | H | NH$_2$ | (+)-isomer |
| 170 | H | H | H | CH$_2$CH$_3$ | H | H | H | 4-OCH$_2$CH$_3$ | H | OH | (+)-isomer |
| 171 | H | H | H | CH$_3$ | H | H | H | 4-CN | H | OH | (−)-isomer |
| 172 | H | H | H | CH$_2$CH$_3$ | H | H | H | 4-CN | H | OH | (−)-isomer |
| 173 | H | H | H | CH$_3$ | H | H | H | 4-CN | H | OH | (+)-isomer |
| 174 | H | H | H | CH$_2$CH$_3$ | H | H | H | 4-Cl | H | OH | (+)-isomer |
| 175 | H | H | H | CH$_2$CH$_3$ | H | H | H | 4-Cl | H | OH | (−)-isomer |
| 176 | H | H | H | CH$_3$ | H | H | H | 4-Cl | H | OH | (+)-isomer |
| 177 | H | H | H | CH$_3$ | H | H | H | 4-Cl | H | OH | (−)-isomer |
| 178 | H | H | H | CH$_3$ | H | H | H | 4-Cl | H | OH | (+)-isomer |
| 179 | H | H | H | CH$_3$ | H | H | H | 4-Cl | H | NH$_2$ | (+)-isomer |
| 180 | H | H | H | CH$_3$ | H | H | H | 4-Cl | H | NH$_2$ | +9.4° (10.1 mg/ml DMSO) |
| 181 | H | H | H | CH$_3$ | H | H | H | H | (4)- 4-methylthiazolyl-2-oxy | OH | |
| 182 | H | H | H | CH$_2$CH$_3$ | H | H | H | H | (4)- 4-methylthiazolyl-2-oxy | OH | |

TABLE-continued

| No. | R1 | R2 | R3 | R4 | R5 | R6 | (R15)n | (R20)n | R21 | Y | m.p. [° C.] |
|---|---|---|---|---|---|---|---|---|---|---|---|
| 183 | H | H | H | CH3 | H | H | H | H | 2-O-(4-methylthiazol-(4)-yl) | OH | |
| 184 | H | H | H | CH2CH3 | H | H | H | H | 2-O-(4-methylthiazol-(4)-yl) | OH | |

Formulations may be prepared analogously to those described in, for example, WO 95/30651.

Biological Examples

*Phytophthora infestans* (late blight of potato/tomato): Tomato leaf disks are placed on water agar in a multiwell plate (24-well format) and sprayed with test solutions. After drying, the leaf disks are inoculated with a spore suspension of the fungus. After appropriate incubation the activity of a compound is assessed 4 dpi (days after inoculation) as preventive fungicidal activity.

Within the tested dose range of 200 to 22 ppm the Compounds No. 078, 079, 080, 081, 082, 083, 084, 088, 099, 100, 102, 105, 107, 108 and 115 inhibited at least 80% of fungal growth.

*Plasmopara viticola* (downy mildew of grapevine): Grape vine leaf disks are placed on agar in a multiwell plate (24-well format) and sprayed with test solutions. After drying, the leaf disks are inoculated with a spore suspension of the fungus. After appropriate incubation the activity of a compound is assessed 7 dpi (days after inoculation) as preventive fungicidal activity.

Within the tested dose range of 200 to 22 ppm the Compounds No. 078, 079, 080, 081, 082, 083, 084, 088, 099, 100, 102, 105, 107, 108 and 115 inhibited at least 80% of fungal growth.

*Erysiphe graminis* f. sp. hordei (Barley powdery mildew): Barley leaf segments are placed on agar in a multiwell plate (24-well format) and sprayed with test solutions. After drying, the leaf disks are inoculated with a spore suspension of the fungus. After appropriate incubation the activity of a compound is assessed 4 dpi (days after inoculation) as preventive fungicidal activity.

Within the tested dose range of 200 to 22 ppm the Compounds No. 079, 092 and 108 inhibited at least 80% of fungal growth.

*Erysiphe graminis* f. sp. tritici (Wheat powdery mildew): Barley leaf segments are placed on agar in a multiwell plate (24-well format) and sprayed with test solutions. After drying, the leaf disks are inoculated with a spore suspension of the fungus. After appropriate incubation the activity of a compound is assessed 4 dpi (days after inoculation) as preventive fungicidal activity.

Within the tested dose range of 200 to 22 ppm the Compounds No. 107 and 108 inhibited at least 80% of fungal growth.

*Pyrenophora teres* (Net blotch): Barley leaf segments are placed on agar in a multiwell plate (24-well format) and sprayed with test solutions. After drying, the leaf disks are inoculated with a spore suspension of the fungus. After appropriate incubation the activity of a compound is assessed 4 dpi (days after inoculation) as preventive fungicidal activity. Within the tested dose range of 200 to 22 ppm the Compound No. 079 inhibited at least 80% of fungal growth.

*Puccinia recondita* (Brown rust): Wheat leaf segments are placed on agar in a multiwell plate (24-well format) and sprayed with test solutions. After drying, the leaf disks are inoculated with a spore suspension of the fungus. After appropriate incubation the activity of a compound is assessed 9 dpi (days after inoculation) as preventive fungicidal activity. Within the tested dose range of 200 to 22 ppm the Compound No. 108 inhibited at least 80% of fungal growth.

*Septoria nodorum* (Glume blotch): Wheat leaf segments are placed on agar in a multiwell plate (24-well format) and sprayed with test solutions. After drying, the leaf disks are inoculated with a spore suspension of the fungus. After appropriate incubation the activity of a compound is assessed 4 dpi (days after inoculation) as preventive fungicidal activity. Within the tested dose range of 200 to 22 ppm the Compound No. 82 inhibited at least 80% of fungal growth.

*Pyricularia oryzae* (Rice blast): Rice leaf segments are placed on agar in a multiwell plate (24-well format) and sprayed with test solutions. After drying, the leaf disks are inoculated with a spore suspension of the fungus. After appropriate incubation the activity of a compound is assessed 4 dpi (days after inoculation) as preventive fungicidal activity. Within the tested dose range of 200 to 22 ppm the Compound No. 115 inhibited at least 80% of fungal growth.

Action Against *Plasmopara Viticola* on Vines

A) Residual-Protective Action

Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95-100% relative humidity and +20° C.

b) Residual-Curative Action

Vine seedlings are infected at the 4- to 5-leaf stage with a sporangia suspension of the fungus. After incubation for 24 hours in a humidity chamber at 95-100% relative humidity and +20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 exhibit a good fungicidal action against *Plasmopara viticola* on vines. Compounds No.: 080, 083, 087, 088, 091, 099, 100, 102 at 200 ppm inhibit fungal infestations in both tests D-1a) and D-1b) by 80-100%. At the same time untreated plants showed pathogen attack of 60-100%.

D-2: Action Against Phytophthora on Tomato Plants a) Residual-protective action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90-100% relative humidity and +20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90-100% relative humidity and +20° C. Compounds of Tables 1 exhibit a good fungicidal action against *Plasmopara viticola* on vines. Compounds No. 078, 080, 082, 083, 087, 088, 099, 100, 102, 108 and 115 at 200 ppm inhibit fungal infestations in both tests D-1a) and D-1b) by 80-100%. At the same time untreated plants showed pathogen attack of 60-100%.

D-3: Action Against Phytophthora on Potato Plants a) Residual-Protective Action 2-3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90-100% relative humidity and +20° C.

b) Systemic Action 2-3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90-100% relative humidity and +20° C. Fungal infestation is effectively controlled with compounds of Table 1.

Compounds No. 087, 088, 100, at 200 ppm inhibit fungal infestations in both tests D-3a) and D-3b) by 60-100%. At the same time untreated plants showed a pathogen attack of 60-100%.

What is claimed is:

1. A compound of formula I:

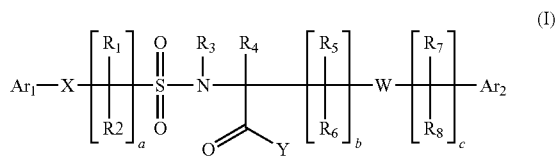

including optical isomers thereof and mixtures of such isomers, wherein:

$Ar_1$ stands for an aryl group which is optionally substituted with n radicals independently selected from $R_{15}$;

$R_{15}$ stands for $C_1$-$C_5$alkyl optionally substituted by halogen, $C_1$-$C_4$alkoxy, —$NR_{16}R_{17}$, —CO—$R_{18}$ or the acyclic or cyclic ketals and acetals of —CO—$R_{18}$;

or $R_{15}$ stands for a —X-linked aryl which is optionally substituted by halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ or the acyclic or cyclic ketals and acetals of —CO—$R_{18}$;

or $R_{15}$ stands for an —X-linked 5- or 6-ring-membered heteroaryl group optionally substituted by halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ or the acyclic or cyclic ketals and acetals of —CO—$R_{18}$;

$R_{16}$ and $R_{17}$ independently of each other stand for hydrogen, $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN;

or $R_{16}$ and $R_{17}$ independently of each other stand for $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN;

or $R_{16}$ and $R_{17}$ independently of each other stand for $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN;

or $R_{16}$ and $R_{17}$ together form a 5-ring-membered non-aromatic carbocyclic ring;

or $R_{16}$ and $R_{17}$ together form a 6-ring-membered non-aromatic carbocyclic ring which is interrupted by —O— or —N($C_1$-$C_5$alkyl)-;

$R_{18}$ stands for $C_1$-$C_5$alkyl optionally substituted by halogen, $C_1$-$C_4$alkoxy, $C_1$-$C_5$alkylamino, di($C_1$-$C_5$alkyl)amino, aryl which in turn is optionally substituted by halogen, $C_1$-$C_5$alkyl, $C_1$-$C_5$haloalkyl, $C_1$-$C_4$alkoxy, —CN, —$NO_2$, $C_1$-$C_5$alkylamino, di($C_1$-$C_5$alkyl)amino or $C_1$-$C_5$alkylcarbonyl, $C_1$-$C_4$alkoxycarbonyl, $C_1$-$C_5$alkylaminocarbonyl or di($C_1$-$C_5$alkyl)aminocarbonyl; or a 5- or 6-ring hetero-aromatic ring which in turn is optionally substituted by halogen, $C_1$-$C_5$alkyl, $C_1$-$C_5$haloalkyl $C_1$-$C_4$alkoxy, —CN, —$NO_2$, $C_1$-$C_5$alkylamino, di($C_1$-$C_5$alkyl)amino, $C_1$-$C_5$alkylcarbonyl, $C_1$-$C_4$alkoxycarbonyl, $C_1$-$C_5$alkylamino carbonyl or di-($C_1$-$C_5$alkyl)amino carbonyl;

or $R_{18}$ stands for $C_3$-$C_6$cycloalkyl optionally substituted by halogen, hydroxy, =O, $C_1$-$C_4$alkoxy, $C_1$-$C_5$alkylamino, or di($C_1$-$C_5$alkyl)amino;

or $R_{18}$ stands for $C_1$-$C_4$alkoxy optionally substituted by halogen, $C_1$-$C_4$alkoxy, $C_1$-$C_5$alkylamino, or di($C_1$-$C_5$alkyl)amino;

or $R_{18}$ stands for phenyl which is optionally substituted by halogen, $C_1$-$C_5$alkyl, $C_1$-$C_5$haloalkyl, $C_1$-$C_4$alkoxy, —CN, —$NO_2$, $C_1$-$C_5$alkylamino, di($C_1$-$C_5$alkyl)amino, $C_1$-$C_5$alkylcarbonyl, $C_1$-$C_4$alkoxycarbonyl, $C_1$-$C_5$alkylamino carbonyl or di-($C_1$-$C_5$alkyl)aminocarbonyl;

or $R_{18}$ stands for a 5- or 6-ring membered heteroaryl comprising nitrogen, oxygen or sulfur as ring members and being optionally substituted by halogen, $C_1$-$C_5$alkyl, $C_1$-$C_5$haloalkyl, $C_1$-$C_4$alkoxy, —CN, —$NO_2$, $C_1$-$C_5$alkylamino, di($C_1$-$C_5$alkyl)amino, $C_1$-$C_5$alkylcarbonyl, $C_1$-$C_4$alkoxycarbonyl, $C_1$-$C_5$alkylaminocarbonyl or di-($C_1$-$C_5$alkyl)aminocarbonyl;

or $R_{15}$ stands for $C_3$-$C_6$cycloalkyl, optionally substituted by halogen, hydroxy, =O, $C_1$-$C_4$alkoxy, or $NR_{16}R_{17}$;

or $R_{15}$ stands for $C_1$-$C_4$alkoxy optionally substituted by halogen, $C_1$-$C_4$alkoxy, —X-aryl which is optionally substituted by halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ or the acyclic or cyclic ketals and acetals of —CO—$R_{18}$; a X-linked-5- or 6-ring-membered heteroaryl group optionally substituted by halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ or the acyclic or cyclic ketals and acetals of —CO—$R_{18}$;

or $R_{15}$ stands for $C_{2-5}$alkenyl optionally substituted by halogen or aryl;

or $R_{15}$ stands for $C_{2-5}$alkynyl optionally substituted by halogen, tri-$C_1$-$C_4$alkyl-silyl or aryl;

or $R_{15}$ stands for $C_{2-5}$alkenyloxy optionally substituted by halogen or aryl;

or $R_{15}$ stands for $C_{2-5}$alkynyloxy optionally substituted by halogen, tri-$C_1$-$C_4$alkyl-silyl or aryl;

or $R_{15}$ stands for $C_3$-$C_6$cycloalkoxy optionally substituted by $C_1$-$C_3$alkyl, halogen or $C_1$-$C_4$alkoxy;

or $R_{15}$ stands for halogen;
or $R_{15}$ stands for $-NR_{16}R_{17}$,
or $R_{15}$ stands for $-NR_2-CO-R_{16}$;
or $R_{15}$ stands for $-NR_2-CO-OR_{16}$;
or $R_{15}$ stands for $-NR_2-CO-NR_{16}R_{17}$;
or $R_{15}$ stands for $-NR_2-CO-SR_{16}$;
or $R_{15}$ stands for $-NR_2-CS-OR_{16}$;
or $R_{15}$ stands for $-NR_2-CS-NR_{16}R_{17}$;
or $R_{15}$ stands for $-NR_2-CS-SR_{16}$;
or $R_{15}$ stands for $-NR_2-C(=N-O-R_{16})-S-OR_{16}$;
or $R_{15}$ stands for $-NR_2-C(=N-O-R_{16})-NR_{16}R_{17}$;
or $R_{15}$ stands for $-NR_2-C(=N-O-R_{16})-SR_{16}$;
or $R_{15}$ stands for $C_1$-$C_5$alkylthio, $C_1$-$C_5$alkylsulfinyl or $C_1$-$C_5$alkylsulfonyl, optionally substituted by halogen;
or $R_{15}$ stands for $-NR_2-SO_2-NR_{16}R_{17}$;
or $R_{15}$ stands for nitro, for cyano or for $-CS-NH_2$;
or $Ar_1$ stands for a 5-ring-membered heteroaryl group comprising as ring members 1 to 4 heteroatoms selected from nitrogen, oxygen or sulfur and in which each ring system may not contain more than one oxygen or sulfur atoms and being optionally substituted with n radicals independently selected from $R_{19}$;
$R_{19}$ is hydrogen, halogen, $C_1$-$C_5$alkyl, $C_1$-$C_5$haloalkyl, $C_1$-$C_4$alkoxy, $-NR_{16}R_{17}$, $-NO_2$, $-CN$, $-CO-R_{18}$ or the acyclic or cyclic ketals and acetals of $-CO-R_{18}$;
or $Ar_1$ stands for a 6-ring-membered heteroaryl group comprising as ring members 1 to 4 nitrogen atoms, and being optionally substituted with n radicals independently selected from $R_{19}$;
$Ar_2$ stands for an aryl group which is optionally substituted with n radicals independently selected from $R_{20}$, wherein $R_{20}$ is as defined as $R_{15}$, and from one radical $R_{21}$;
$R_{21}$ stands for hydrogen;
or $R_{21}$ stands for $-X$-aryl which is optionally substituted by halogen, $C_1$-$C_5$alkyl, $C_1$-$C_5$haloalkyl, $C_1$-$C_4$alkoxy, $-CN$, $-NO_2$, $-NR_{16}R_{17}$, $-CO-R_{18}$ or the acyclic or cyclic ketals and acetals of $-CO-R_{18}$;
or $R_{21}$ stands for an $-X$-linked 5-membered aromatic or non-aromatic heterocyclic ring comprising nitrogen, oxygen or sulfur as ring members and being optionally substituted by halogen, $C_1$-$C_5$alkyl, $C_1$-$C_5$haloalkyl, $C_1$-$C_4$alkoxy, $-CN$, $-NO_2$, $-NR_{16}R_{17}$, $-CO-R_{18}$ or the acyclic or cyclic ketals and acetals of $-CO-R_{18}$;
or $R_{21}$ stands for a X-linked 6-membered aromatic or non-aromatic heterocyclic ring comprising nitrogen, oxygen or sulfur as ring members and being optionally substituted by halogen, $C_1$-$C_5$alkyl, $C_1$-$C_5$haloalkyl, $C_1$-$C_4$alkoxy, $-CN$, $-NO_2$, $-NR_{16}R_{17}$, $-CO-R_{18}$ or the acyclic or cyclic ketals and acetals of $-CO-R_{18}$;
or $R_{21}$ stands for $-CO-R_{18}$ or the acyclic or cyclic ketals and acetals of $-CO-R_{18}$;
or $R_{21}$ stands for $-O-CO-R_{18}$;
or $R_{21}$ stands for $-C(=N-O-R_{16})-R_{18}$;
or $R_{21}$ and one $R_{20}$ together form a 3- or 4-membered non-aromatic bridge forming an annellated ring which may contain a carbonyl function or nitrogen, oxygen or sulfur as ring members and is optionally substituted by $C_1$-$C_3$alkyl;
or $Ar_2$ stands for a 5-ring-membered heteroaryl group comprising as ring members 1 to 4 heteroatoms selected from nitrogen, oxygen or sulfur and in which each ring system may not contain more than 1 oxygen or sulfur atoms and being optionally substituted with n radicals independently selected from $R_{19}$;
or $Ar_2$ stands for a 6-ring-membered heteroaryl group comprising as ring members 1 to 4 nitrogen atoms, and being optionally substituted with n radicals independently selected from $R_{19}$;
or $Ar_2$ stands for a fused bicyclic heteroaryl group comprising as ring members 1 to 4 heteroatoms selected from nitrogen, oxygen or sulfur, and being composed from the 5-ring- or b-ring-membered heteroaryl groups as defined for $Ar_2$ with an annellated phenyl ring or with an annellated second 6-ring-membered heteroaryl, each ring and the bicyclic heteroaryl being optionally substituted with n radicals independently selected from $R_{19}$;
each n is independently a number ranging from (i) zero to (ii) a number equal to the number of respective ring members minus one;
$R_1$ and $R_2$ stand independently of each other for hydrogen; $C_1$-$C_5$alkyl optionally substituted by halogen, $C_1$-$C_3$alkoxy or $-NR_{16}R_{17}$; $C_2$-$C_5$alkenyl optionally substituted by halogen or $C_1$-$C_3$alkoxy; $C_2$-$C_5$alkynyl; $C_3$-$C_6$cycloalkyl optionally substituted by halogen, $C_1$-$C_3$alkoxy; $C_1$-$C_3$alkyl or $-NR_{16}R_{17}$;
$R_3$ stands for hydrogen; $C_3$-$C_5$alkenyl; $C_3$-$C_5$alkynyl; or $C_1$-$C_3$alkyl optionally substituted by $C_1$-$C_3$alkoxy; $C_3$-$C_5$alkenyloxy or $C_3$-$C_5$alkynyloxy;
$R_4$ is $C_1$-$C_5$-alkyl optionally substituted by halogen, $C_1$-$C_3$alkoxy or $-NR_{16}R_{17}$; $C_2$-$C_5$alkenyl optionally substituted by halogen or $C_1$-$C_3$alkoxy; $C_2$-$C_5$alkynyl; or $C_3$-$C_6$cycloalkyl optionally substituted by halogen, $C_1$-$C_3$alkoxy or $C_1$-$C_3$alkyl;
$R_5$ and $R_6$ are independently of each other hydrogen; $C_1$-$C_5$alkyl optionally substituted by halogen, $C_1$-$C_3$alkoxy or $-NR_{16}R_{17}$; $C_2$-$C_5$alkenyl optionally substituted by halogen or $C_1$-$C_3$alkoxy; $C_2$-$C_5$alkynyl; $C_3$-$C_6$cycloalkyl optionally substituted by halogen, $C_1$-$C_3$alkoxy, $C_1$-$C_3$alkyl or $-NR_{16}R_{17}$;
$R_7$ and $R_8$ are independently of each other hydrogen; $C_1$-$C_5$alkyl optionally substituted by halogen, $C_1$-$C_3$alkoxy or $-NR_{16}R_{17}$; $C_2$-$C_5$alkenyl optionally substituted by halogen or $C_1$-$C_3$alkoxy; $C_2$-$C_5$alkynyl; $C_3$-$C_6$cycloalkyl optionally substituted by halogen, $C_1$-$C_3$alkoxy, $C_1$-$C_3$alkyl or $-NR_{16}R_{17}$;
W designates a bridge selected from $-O-$, $-S-$, $-SO-$, $-SO_2-$ or is an $-NH-$ or $-N(C_1$-$C_5$alkyl)-bridge;
X designates a direct bond or a bridge selected from $-O-$, $-S-$, $-SO-$, $-SO_2-$ or is an $-NH-$ or $-N(C_1$-$C_5$alkyl)-bridge;
Y designates $-OR_9$ or $NR_{10}R_{11}$;
a and b independently of each other stand for a number 1, 2 or 3; and
c stands for a number zero, 1 or 2;
$R_9$ designates hydrogen, $C_1$-$C_5$alkyl, $C_3$-$C_5$alkenyl, $C_3$-$C_5$alkynyl, phenyl or halogen substituted phenyl;
$R_{10}$ and $R_{11}$ independently of each other stand for hydrogen; $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or $-CN$; $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or $-CN$; $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or —NH—CH($R_{12}$)CO—Z;

or $R_{10}$ and $R_{11}$ together form a 5-ring-membered non-aromatic heterocyclic ring; or together form a 6-ring-membered non-aromatic heterocyclic ring which is interrupted by —O—, —S— or —N($C_1$-$C_5$alkyl)-;

$R_{12}$ designates $C_1$-$C_5$alkyl optionally substituted by halogen $C_1$-$C_5$haloalkyl or aryl which in turn is optionally substituted by halogen, $C_1$-$C_5$alkyl, $C_1$-$C_5$haloalkyl, $C_1$-$C_4$alkoxy, hydroxy or —CN;

Z is —$OR_9$ or $NR_{13}R_{14}$;

$R_{13}$ and $R_{14}$ independently of each other stand for hydrogen; $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN;

or $R_{13}$ and $R_{14}$ together form a 5-ring-membered non-aromatic carbocyclic ring; or together form a 6-ring-membered non-aromatic carbocyclic ring which is interrupted by —O—, —S— or —N($C_1$-$C_5$alkyl)-.

2. A compound according to claim 1, wherein $Ar_1$ and $Ar_2$ independently of each other stand for optionally substituted phenyl;

or the optional substituents $R_{15}$ of $Ar_1$ are each independently selected from the group consisting of halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN and —CO—$R_{18}$;

or the optional substituents $R_{20}$ of $Ar_2$ are each independently selected from the group consisting of halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN, —CO—$R_{18}$, —$NR_{16}R_{17}$, —$NR_2$—CO—$R_{16}$, —$NR_2$—CO—$OR_{16}$, —$NR_2$—CO—$NR_{16}R_{17}$, —$NR_2$—CO—$SR_{16}$, —$NR_2$—CS—$OR_{16}$, —$NR_2$—CS—$NR_{16}R_{17}$, —$NR_2$—CS—$SR_{16}$, $C_1$-$C_5$alkylthio, $C_1$-$C_5$alkylsulfinyl, $C_1$-$C_5$alkylsulfonyl, $C_1$-$C_5$haloalkylthio, $C_1$-$C_5$haloalkylsulfinyl, $C_1$-$C_5$haloalkylsulfonyl, —$NR_2$—$SO_2$—$NR_{16}R_{17}$, nitro, cyano and —CS—$NH_2$; and the optional substituent $R_{21}$ on $Ar_2$ is selected from phenyl, imidazolyl, thiazolyloxy, pyridyloxy, pyridyl, pyrimidinyloxy, pyrimidinyl, oxadiazolyl, triazolyl, pyrazolyl, oxadiazolyloxy, triazolyloxy and pyrazolyloxy, each group $Ar_2$ being optionally substituted by $C_1$-$C_5$alkyl optionally substituted by halogen, $C_1$-$C_4$alkoxy optionally substituted by halogen, cyano, nitro, amino, aryl optionally substituted by halogen, heteroaryl optionally substituted by halogen, and phenyl optionally substituted by halogen, the preceding groups optionally substituted by halogen comprising one or more identical or different halogen atoms when halogen is present; alkoxy; alkenyloxy; alkynyloxy; alkoxyalkyl; haloalkoxy, alkylthio; haloalkylthio; alkyl-sulfonyl; formyl; alkanoyl; hydroxy; halogen; cyano; nitro; amino; hydroxy, alkylamino; dialkyl-amino; carboxyl; alkoxycarbonyl; alkenyloxycarbonyl; or alkynyloxycarbonyl;

or the optional substituent $R_{21}$ on $Ar_2$ is selected from halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ and the acyclic or cyclic ketals and acetals of —CO—$R_{18}$;

or the optional substituent $R_{21}$ on $Ar_2$ is selected from —CO—$R_{18}$, —O—CO—$R_{18}$, phenyl, phenoxy, imidazolyl, imidazolyloxy, thiazolyloxy, thiazolyl, thiadiazolyloxy, thiadiazolyl, pyridyloxy, pyridyl, pyrimidinyloxy, pyrimidinyl, oxadiazolyl, oxadiazolyloxy, triazolyl, pyrazolyl, triazolyloxy and pyrazolyloxy, each phenyl or heteroaryl group being optionally substituted by $C_1$-$C_5$alkyl optionally substituted by halogen, $C_1$-$C_4$alkoxy optionally substituted by halogen, cyano, nitro, amino, aryl optionally substituted by halogen, heteroaryl optionally substituted by halogen, and phenyl optionally substituted by halogen, the preceding groups optionally substituted by halogen comprising one or more identical or different halogen atoms when halogen is present; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; hydroxy, alkylamino; dialkylamino; carboxyl; alkoxycarbonyl; alkenyloxycarbonyl; or alkynyloxycarbonyl;

or the optional substituent $R_{21}$ on $Ar_2$ is selected from —CO—$C_1$-$C_5$alkyl, —O—CO—$C_1$-$C_5$alkyl and —CO—$C_1$-$C_4$alkoxy;

or the optional substituent $R_{21}$ on $Ar_2$ is selected from dimethylaminocarbonyl, acetyl, propionyl, acetoxy, methoxycarbonyl, ethoxycarbonyl, benzoyl, methoximinoethyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dichloropyridyloxy), 2-(4,6-dimethoxypyrimidinylthio), 2-oxadiazolyl, 2-(5-methyl-oxadiazolyl), 2-(5-ethyl-oxadiazolyl), 1-triazolyl, 1-pyrazolyl, 1-(3,4-dimethylpyrazolyl), 4-(2-methylthiazolyl), 2-(1,3,4-oxadiazolyl), N-pyrrolidin-2-onyl, and 2-quinoxalinyl; and $R_1$, $R_2$, $R_5$, $R_6$, $R_7$ and $R_8$ independently of each other stand for hydrogen or methyl;

or $R_1$ and $R_5$ are independently of each other $C_1$-$C_5$alkyl and $R_2$ and $R_6$ are hydrogen;

or $R_3$ is hydrogen or $C_1$-$C_3$alkyl optionally substituted with $C_1$-$C_4$alkoxy, $C_3$-$C_4$alkenyloxy, or $C_3$-$C_4$alkynyloxy;

or $R_4$ is hydrogen or $C_1$-$C_5$alkyl optionally substituted with halogen, $C_1$-$C_3$alkoxy;

or $R_4$ is $C_1$-$C_5$alkyl or $C_1$-$C_5$haloalkyl;

or Y stands for O—$R_9$, where $R_9$ is hydrogen, $C_1$-$C_5$alkyl, $C_3$-$C_5$alkenyl, $C_3$-$C_5$alkynyl, phenyl, or 4-halogenophenyl;

$R_{10}$ and $R_{11}$ independently of each other stand for hydrogen, $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN;

or $R_{10}$ and $R_{11}$ independently of each other stand for $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN;

or $R_{10}$ and $R_{11}$ independently of each other stand for $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for a group —NH—CH($R_{12}$)CO—Z;

or $R_{10}$ and $R_{11}$ together form a 5-ring-membered non-aromatic heterocyclic ring;

or $R_{10}$ and $R_{11}$ together form a 6-ring-membered non-aromatic heterocyclic ring which is interrupted by —O—, —S— or —N($C_1$-$C_5$alkyl)-;

$R_{12}$ designates $C_1$-$C_5$alkyl optionally substituted by halogen, $C_1$-$C_5$haloalkyl or aryl which in turn is optionally substituted by halogen, $C_1$-$C_5$alkyl, $C_1$-$C_5$haloalkyl, $C_1$-$C_4$alkoxy, hydroxy or —CN;

Z is —$OR_9$ or $NR_{13}R_{14}$;

$R_{13}$ and $R_{14}$ independently of each other stand for hydrogen, $C_1$-$C_5$alkyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN;

or $R_{13}$ and $R_{14}$ stand for $C_3$-$C_5$alkynyl optionally substituted by halogen, $C_1$-$C_5$haloalkyl, $C_1$-$C_4$alkoxy, $C_1$-$C_5$alkylamino, di($C_1$-$C_5$alkyl)amino, or aryl which in turn is optionally substituted by halogen, $C_1$-$C_5$alkyl, $C_1$-$C_5$haloalkyl, $C_1$-$C_4$alkoxy or —CN;

or $R_{13}$ and $R_{14}$ together form a 5-ring-membered non-aromatic carbocyclic ring;

or $R_{13}$ and $R_{14}$ together form a 6-ring-membered non-aromatic carbocyclic ring which is interrupted by —O—, —S— or —N($C_1$-$C_5$alkyl)-;

W is —O—;

X is a direct bond;

Of the suffixes (a) and (b) designate the number 1; and the suffix (c) stands for the number zero.

3. A compound according to claim 1, wherein $Ar_1$ and $Ar_2$ independently of each other stand for optionally substituted phenyl;

and the optional substituents $R_{15}$ of $Ar_1$ are each independently selected from the group consisting of halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN and —CO—$R_{18}$;

and the optional substituents $R_{20}$ of $Ar_2$ are each independently selected from the group consisting of halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN, —CO—$R_{18}$, —$NR_{16}R_{17}$, —$NR_2$—CO—$R_{16}$, —$NR_2$—CO—$OR_{16}$, —$NR_2$—CO—$NR_{16}R_{17}$, —$NR_2$—CO—$SR_{16}$, —$NR_2$—CS—$OR_{16}$, —$NR_2$—CS—$NR_{16}R_{17}$, —$NR_2$—CS—$SR_{16}$, $C_1$-$C_5$alkylthio, $C_1$-$C_5$alkylsulfinyl, $C_1$-$C_5$alkylsulfonyl, $C_1$-$C_5$haloalkylthio, $C_1$-$C_5$haloalkylsulfinyl, $C_1$-$C_5$haloalkylsulfonyl, —$NR_2$—$SO_2$—$NR_{16}R_{17}$, nitro, cyano and —CS—$NH_2$;

and the optional substituent $R_{21}$ on $Ar_2$ is selected from phenyl, imidazolyl, thiazolyloxy, pyridyloxy, pyridyl, pyrimidinyloxy, pyrimidinyl, oxadiazolyl, triazolyl, pyrazolyl, oxadiazolyloxy, triazolyloxy and pyrazolyloxy, each group $R_{21}$ being optionally substituted by $C_1$-$C_5$alkyl optionally substituted by halogen, $C_1$-$C_4$alkoxy optionally substituted by halogen, cyano, nitro, amino, aryl optionally substituted by halogen, heteroaryl optionally substituted by halogen, and phenyl optionally substituted by halogen, the preceding groups optionally substituted by halogen comprising one or more identical or different halogen atoms when halogen is present; alkoxy; alkenyloxy; alkynyloxy; alkoxyalkyl; haloalkoxy, alkylthio; haloalkylthio; alkyl-sulfonyl; formyl; alkanoyl; hydroxy; halogen; cyano; nitro; amino; hydroxy, alkylamino; dialkyl-amino; carboxyl; alkoxycarbonyl; alkenyloxycarbonyl; or alkynyloxycarbonyl.

4. A compound according to claim 1 wherein $Ar_1$ and $Ar_2$ independently stand for optionally substituted aryl groups;

and the optional substituents $R_{15}$ of $Ar_1$ are each independently selected from the group consisting of halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN and —CO—$R_{18}$;

and the optional substituents $R_{20}$ of $Ar_2$ are each independently selected from the group consisting of halogen, $C_1$-$C_5$alkyl, $C_1$-$C_5$haloalkyl, $C_1$-$C_4$alkoxy, $C_1$-$C_4$haloalkoxy, $C_3$-$C_6$cycloalkyl, —CN, —CO—$R_{18}$, —$NR_{16}R_{17}$, —$NR_2$—CO—$R_{16}$, —$NR_2$—CO—$OR_{16}$, —$NR_2$—CO—$NR_{16}R_{17}$, —$NR_2$—CO—$SR_{16}$, —$NR_2$—CS—$OR_{16}$, —$NR_2$—CS—$NR_{16}R_{17}$, —$NR_2$—CS—$SR_{16}$, $C_1$-$C_5$alkylthio, $C_1$-$C_5$alkylsulfinyl, $C_1$-$C_5$alkylsulfonyl, $C_1$-$C_5$haloalkylthio, $C_1$-$C_5$haloalkylsulfinyl, $C_1$-$C_5$haloalkylsulfonyl, —$NR_2$—$SO_2$—$NR_{16}R_{17}$, nitro, cyano and —CS—$NH_2$;

and the optional substituent $R_{21}$ on $Ar_2$ is selected from halogen, $C_1$-$C_5$alkyl, $C_1$-$C_5$haloalkyl, $C_1$-$C_4$alkoxy, —CN, —$NO_2$, —$NR_{16}R_{17}$, —CO—$R_{18}$ and the acyclic or cyclic ketals and acetals of —CO—$R_{18}$; —O—CO—$R_{18}$, phenyl, imidazolyl, thiazolyloxy, pyridyloxy, pyridyl, pyrimidinyloxy, pyrimidinyl, oxadiazolyl, triazolyl, pyrazolyl, oxadiazolyloxy, triazolyloxy and pyrazolyloxy, each phenyl or heteroaryl group being optionally substituted by $C_1$-$C_5$alkyl optionally substituted by halogen, $C_1$-$C_4$alkoxy optionally substituted by halogen, cyano, nitro, amino, aryl optionally substituted by halogen, heteroaryl optionally substituted by halogen, and phenyl optionally substituted by halogen the preceding groups optionally substituted by halogen comprising one or more identical or different halogen atoms when halogen is present; alkoxy; alkenyloxy; alkynyloxy; alkoxyalkyl; haloalkoxy, alkylthio; haloalkylthio; alkyl-sulfonyl; formyl; alkanoyl; hydroxy; halogen; cyano; nitro; amino; hydroxy, alkylamino; dialkylamino; carboxyl; alkoxycarbonyl; alkenyloxycarbonyl; or alkynyloxycarbonyl;

and $R_1$, $R_2$, $R_5$, $R_6$, $R_7$ and $R_8$ independently of each other are hydrogen or methyl;

and $R_3$ is hydrogen or $C_1$-$C_3$alkyl optionally substituted with $C_1$-$C_4$alkoxy, $C_3$-$C_4$alkenyloxy, or $C_3$-$C_4$alkynyloxy;

and $R_4$ is $C_1$-$C_5$alkyl optionally substituted with halogen, $C_1$-$C_3$alkoxy, $C_1$-$C_3$alkylamino or di-$C_1$-$C_3$alkylamino;

and W is —O—;

and Y is $OR_9$, where $R_9$ is hydrogen, $C_1$-$C_5$alkyl; $C_3$-$C_5$alkenyl, $C_3$-$C_5$alkynyl, 4-halogenophenyl;

or Y is $NR_{10}R_{11}$ and $R_{10}$ and $R_{11}$ independently of each other, stand for hydrogen, $C_1$-$C_5$alkyl, or aryl which in turn is optionally substituted by halogen, $C_1$-$C_5$alkyl, $C_1$-$C_5$haloalkyl, $C_1$-$C_4$alkoxy or —CN;

or $R_{10}$ and $R_{11}$ stand for $C_3$-$C_5$alkenyl;

or $R_{10}$ and $R_{11}$ stand for $C_3$-$C_5$alkynyl;

or $R_{10}$ and $R_{11}$ stand for a group —NH—CH($R_{12}$)CO—Z;
or $R_{10}$ and $R_{11}$ together form a 5-ring-membered non-aromatic heterocyclic ring;
or $R_{10}$ and $R_{11}$ together form a 6-ring-membered non-aromatic heterocyclic ring which is interrupted by —O—, —S— or —N($C_1$-$C_5$alkyl)-;
$R_{12}$ designates $C_1$-$C_5$alkyl;
Z is —$OR_9$, or $NR_{13}R_{14}$;
$R_{13}$ and $R_{14}$ independently of each other, stand for hydrogen, $C_1$-$C_5$alkyl, or aryl which in turn is optionally substituted by halogen, $C_1$-$C_5$alkyl, $C_1$-$C_5$haloalkyl, $C_1$-$C_4$alkoxy or —CN; or stand for $C_3$-$C_5$alkenyl; or stand for $C_3$-$C_5$alkynyl; or
$R_{13}$ and $R_{14}$ together form a 5-ring-membered non-aromatic carbocyclic ring; or together form a 6-ring-membered non-aromatic carbocyclic ring which is interrupted by —O—, —S— or —N($C_1$-$C_5$alkyl)-;
X is a direct bond; and
the suffixes (a) and (b) designate the number 1; and
the suffix (c) stands for the number zero.

5. A compound according to claim 1 wherein $Ar_1$ and $Ar_2$ independently of each other stand for optionally substituted phenyl;
and the optional substituents $R_{15}$ and $R_{20}$ of $Ar_1$ and $Ar_2$ are each independently selected from the group consisting of $C_1$-$C_5$alkyl, $C_1$-$C_5$haloalkyl, $C_1$-$C_4$alkoxy, $C_1$-$C_4$haloalkoxy and $C_3$-$C_6$cycloalkyl;
and the optional substituent $R_{21}$ on $Ar_2$ is selected from —CO—$C_1$-$C_5$alkyl, —CO—$C_1$-$C_4$alkoxy, —O—CO—$C_1$-$C_5$alkyl, phenyl, phenoxy, imidazolyl, imidazolyloxy, thiazolyl-oxy, thiazolyl, thiadiazolyloxy, thiadiazolyl, pyridyloxy, pyridyl, pyrimidinyloxy, pyrimidinyl, oxadiazolyl, oxadiazolyloxy, triazolyl, pyrazolyl, triazolyloxy and pyrazolyloxy, each phenyl or heteroaryl group being optionally substituted by $C_1$-$C_5$alkyl optionally substituted by halogen, $C_1$-$C_4$alkoxy optionally substituted by halogen, cyano, nitro, amino, aryl optionally substituted by halogen, heteroaryl optionally substituted by halogen, and phenyl optionally substituted by halogen and phenyl alkyl, it being possible in turn for all of the preceding groups optionally substituted by halogen comprising one or more identical or different halogen atoms when halogen is present; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; hydroxy, alkylamino; dialkylamino; carboxyl; alkoxycarbonyl; alkenyloxycarbonyl; or alkynyloxycarbonyl;
and $R_1$ and $R_5$ are independently $C_1$-$C_5$alkyl;
and $R_2$ and $R_6$ are hydrogen;
and $R_3$ is hydrogen, $C_1$-$C_3$alkyl or $C_1$-$C_4$alkoxy-$C_1$-$C_3$alkyl;
and $R_4$ is $C_1$-$C_5$alkyl or $C_1$-$C_5$haloalkyl;
and W is —O—;
and Y is $OR_9$, where $R_9$ is hydrogen, $C_1$-$C_5$alkyl, $C_3$-$C_5$alkenyl, $C_3$-$C_5$alkynyl, or 4-halogenophenyl;
X is a direct bond;
and the suffixes (a) and (b) designate the number 1;
and the suffix (c) stands for the number zero.

6. A compound according to claim 1 wherein $Ar_1$ and $Ar_2$ independently of each other stand for optionally substituted phenyl;
and the optional substituents $R_{15}$ and $R_{20}$ of $Ar_1$ and $Ar_2$ are each independently selected from the group consisting of bromo, chloro, fluoro, iodo, cyano, hydroxy, amino, nitro, methyl, ethyl, propyl, isopropyl, methoxy, ethoxy, propoxy, isopropoxy, allyloxy, propargyloxy, benzyloxy, trifluoromethyl, trifluoromethoxy, 2-cyano-2-methyl-butyloxy, methylsulfonyl, methylsulfinyl, methylthio, cyclopentyl, cyclohexyl, methoximinoethyl, aminocarbonyl, butylcarbonylamino, tert-butylcarbonylamino, triazol-1-ylmethyl, 1,2,4-triazol-1-ylmethyl, N-morpholinocarbonylamino, aminocarbonyloxyethoxy, morpholinocarbonyloxyethoxy and cyanopyridyloxyethoxy;
and the optional substituent $R_{21}$ on $Ar_2$ is selected from aminocarbonyl, dimethylaminocarbonyl, acetyl, propionyl, acetoxy, methoxycarbonyl, ethoxycarbonyl, benzoyl, methoximinoethyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dichloropyridyloxy), 2-(4,6-dimethoxypyrimidinylthio), 2-oxadiazolyl, 2-(5-methyl-oxadiazolyl), 2-(5-ethyl-oxadiazolyl), 1-triazolyl, 1-pyrazolyl, 1-(3,4-dimethylpyrazolyl), 4-(2-methylthiazolyl), 2-(1,3,4-oxadiazolyl), N-pyrrolidin-2-onyl, and 2-quinoxalinyl;
and $R_1$ and $R_5$ are each independently $C_1$-$C_5$alkyl;
and $R_2$ and $R_6$ are hydrogen;
and $R_3$ is hydrogen, $C_1$-$C_3$alkyl or $C_1$-$C_4$alkoxy-$C_1$-$C_3$alkyl;
and $R_4$ is $C_1$-$C_5$alkyl or $C_1$-$C_5$haloalkyl;
and W is —O—;
and Y is $OR_9$, where $R_9$ is hydrogen, $C_1$-$C_5$alkyl, $C_3$-$C_5$alkenyl, $C_3$-$C_5$alkynyl, or 4-halogenophenyl;
X is a direct bond;
and the suffixes (a) and (b) designate the number 1;
and the suffix (c) stands for the number zero.

7. A compound according to claim 1 wherein $Ar_1$ and $Ar_2$ independently of each other stand for optionally substituted phenyl;
and the optional substituents $R_{15}$ and $R_{20}$ of $Ar_1$ and $Ar_2$ are each independently selected from the group consisting of bromo, chloro, fluoro, methyl, ethyl, methoxy, ethoxy, trifluoromethyl and trifluoromethoxy;
and the optional substituent $R_{21}$ on $Ar_2$ is selected from acetyl, methoxycarbonyl, ethoxycarbonyl, 1-imidazolyl, 5-(3-methyl-1,2,4-thiadiazolyloxy), 2-pyridyl, 2-pyridyloxy, 4-pyrimidinyl, 2-(3,5-dichloropyridyloxy), 2-(4,6-dimethoxypyrimidinylthio), 2-oxadiazolyl, 2-(5-methyl-oxadiazolyl), 2-(5-ethyl-oxadiazolyl), 1-(1,2,4-triazolyl), 1-pyrazolyl, 4-(2-methylthiazolyl), 2-(1,3,4-oxadiazolyl), and N-pyrrolidin-2-onyl;
and $R_1$ and $R_5$ are methyl;
and $R_2$ and $R_6$ are hydrogen;
and $R_3$ is hydrogen, methyl, ethyl, propyl, ethoxymethyl or methoxymethyl;
and $R_4$ is methyl, ethyl, propyl or fluoromethyl;
and W is —O—;
and Y is $OR_9$, where $R_9$ is hydrogen, $C_1$-$C_5$alkyl or halogenophenyl;
or Y is $NR_{10}R_{11}$;
X is a direct bond; and
the suffixes (a) and (b) designate the number 1; and
the suffix (c) stands for the number zero.

8. A compound according to claim 1 selected from the group consisting of
2,N-Dimethyl-2-phenylmethanesulfonylamino-3-(-[1,2,4]triazol-1-yl-phenoxy)-propionamide,
2-Methyl-2-phenylmethanesulfonylamino-3-(4-[1,2,4]triazol-1-yl-phenoxy)-propionic acid methyl ester,
2-Methyl-2-phenylmethanesulfonylamino-3-(4-[1,2,4]triazol-1-yl-phenoxy)-propionamide, 2-Methyl-2-phenylmethanesulfonylamino-3-(4-[1,2,4]triazol-1-yl-phenoxy)-propionic acid,
N-(4-Chloro-phenyl)-2-methyl-2-phenylmethanesulfonylamino-3-(4-[1,2,4]triazol-1-yl-phenoxy)-propionamide,
N-(3-Trifluoro-phenyl)-2-methyl-2-phenylmethanesulfonylamino-3-(4-[1,2,4]triazol-1-yl-phenoxy)-propionamide,
N-(1-Phenyl-ethyl)-2-methyl-2-phenylmethanesulfonylamino-3-(4-[1,2,4]triazol-1-yl-phenoxy)-propionamide,
N-[2-(3,4-Dimethoxy-phenyl)-ethyl]-2-methyl-2-phenylmethanesulfonylamino-3-(4-[1,2,4]triazol-1-yl-phenoxy)-propionamide,
3-(4-Ethoxy-phenoxy)-2,N-dimethyl-2-phenylmethanesulfonylamino-propionamide,
3-(4-Ethoxy-phenoxy)-2-methyl-N-(1-phenyl-ethyl)-2-phenylmethanesulfonylamino-propionamide,
3-(4-Ethoxy-phenoxy)-2-methyl-N-(4-methoxy-benzyl)-2-phenylmethanesulfonylamino-propionamide,
2-(4-Ethoxy-phenoxymethyl)-2-phenylmethanesulfonylamino-butyramide,
3-(4-Ethoxy-phenoxy)-2-methyl-N-[2-(3,4-dimethoxy-phenyl)-ethyl]-2-phenylmethanesulfonylamino-propionamide,
3-(4-Ethoxy-phenoxy)-2,N,N-trimethyl-2-phenylmethanesulfonylamino-propionamide,
3-(4-Ethoxy-phenoxy)-2-methyl-2-phenylmethanesulfonylamino-N-prop-2-ynyl-propionamide,
3-(4-Ethoxy-phenoxy)-2-methyl-2-phenylmethanesulfonylamino-1-morpholin-4-yl-propan-1-one,
3-(4-Ethoxy-phenoxy)-N-methoxy-2,N-dimethyl-2-phenylmethanesulfonylamino-propionamide,
N-Methoxy-2-methyl-2-phenylmethanesulfonylamino-3-(4-[1,2,4]triazol-1-yl-phenoxy)-propionamide,
N-(-1-Ethynyl-cyclohexyl)-2-methyl-2-phenylmethanesulfonylamino-3-(4-[1,2,4]triazol-1-yl-phenoxy)-propionamide, and
3-(4-Ethoxy-phenoxy)-2-methyl-2-phenylmethanesulfonylamino-propionic acid methyl ester.

9. A process for the preparation of the compound of claim 1, said process comprising:
a) reacting the sulfonylating agent of formula II:

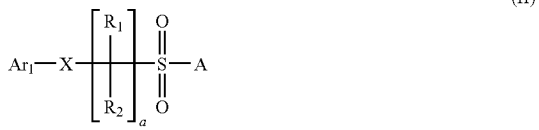

(II)

wherein $Ar_1$, a, X and $R_1$ to $R_2$, are defined as under formula I, and A stands for a leaving group of the structure
—O—SO$_2$—(CR$_1$R$_2$)$_a$—X—Ar$_1$  or  —O—CO—C$_1$-C$_5$alkyl, with an amino-acetonitrile of formula III:

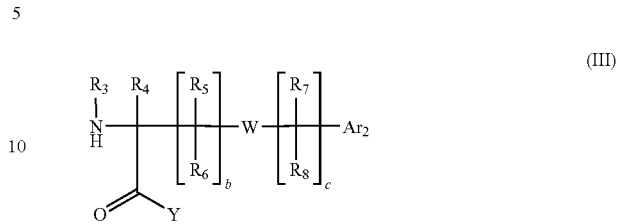

(III)

wherein $Ar_2$, b, c, W, Y and $R_3$ to $R_8$, are defined as under formula I, or
b) reacting the compound of formula V:

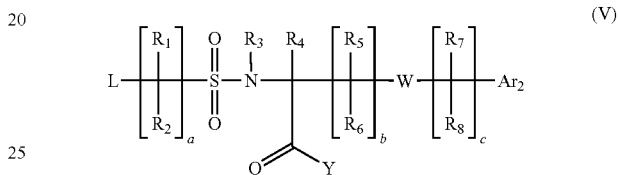

(V)

wherein $Ar_2$, a, b, c, W, y and $R_1$ to $R_8$ are defined as under formula I and L is a leaving group, with a compound of formula Ar$_1$—X' wherein $Ar_1$ is defined as under formula I and X' is either an anionic radical species of X combined with an alkaline- or earthalkaline—metal cation as counterion or is defined as X—H.

10. A composition for controlling and protecting against phytopathogenic microorganisms, said composition comprising the compound of claim 1.

11. A method of controlling an infestation of crop plants by phytopathogenic microorganisms, said method comprising the application of the compound of claim 1 as an active ingredient to the plant, to parts of plants or to the locus thereof.

12. A method according to claim 11, wherein the phytopathogenic microorganisms are fungal organisms.

13. A process according to claim 9, wherein L comprises a halogen.

14. A process according to claim 9, wherein L comprises a sulfonyloxy group.

* * * * *